(12) United States Patent
Masters

(10) Patent No.: US 6,342,250 B1
(45) Date of Patent: Jan. 29, 2002

(54) DRUG DELIVERY DEVICES COMPRISING BIODEGRADABLE PROTEIN FOR THE CONTROLLED RELEASE OF PHARMACOLOGICALLY ACTIVE AGENTS AND METHOD OF MAKING THE DRUG DELIVERY DEVICES

(75) Inventor: David B. Masters, Hastings, MN (US)

(73) Assignee: Gel-Del Technologies, Inc., Saint Paul, MN (US)

( * ) Notice: Subject to any disclaimer, the term of this patent is extended or adjusted under 35 U.S.C. 154(b) by 0 days.

(21) Appl. No.: 09/160,421

(22) Filed: Sep. 25, 1998

Related U.S. Application Data

(60) Provisional application No. 60/060,048, filed on Sep. 25, 1997.

(51) Int. Cl.[7] .............................. A61K 9/10; A61K 9/22; A61K 9/70; A61K 47/42
(52) U.S. Cl. ........................ 424/484; 424/468; 424/443
(58) Field of Search ................................ 424/486, 484, 424/464–465, 468, 489, 400, 443

(56) References Cited

U.S. PATENT DOCUMENTS

| | | | |
|---|---|---|---|
| 4,474,752 A | 10/1984 | Haslam et al. | 424/78 |
| 4,959,217 A | 9/1990 | Sanders et al. | 424/473 |
| 5,041,292 A | 8/1991 | Feijen | 424/484 |
| 5,188,837 A | 2/1993 | Domb | 424/450 |
| 5,324,775 A | 6/1994 | Rhee et al. | 525/54.2 |
| 5,573,934 A | 11/1996 | Hubbell et al. | 435/177 |
| 5,665,428 A | 9/1997 | Cha et al. | 427/213.3 |
| 5,700,478 A | * 12/1997 | Biegajski et al. | |
| 5,773,019 A | 6/1998 | Ashton et al. | 424/423 |

OTHER PUBLICATIONS

Masters et al., Liposphere Local Anesthetic Timed–Release for Perineural Site Application, Pharmaceutical Research, vol. 15, No. 7, 1998, pp. 1038–1045.
Ghandehari et al., Genetic Engineering of Protein–Based Polymers: Potential in Controlled Drug Delivery, Pharmaceutical Research, vol. 15, No. 6, 1998, pp. 813–815.
Masters, Letter to Joseph Cappello, Jul. 1, 1996.
Skarda et al., Biodegradable Hydrogel for Controlled Release of Biologically Active Macromolecules, Journal of Bioactive and Compatible Polymers, vol. 8, Jan. 1993, pp. 24–40.
Lee, J. Controlled Release, 2, 277 (1985).
Heller et al., Controlled release of water–soluble macromolecules from bioerodible hydrogels, Biomaterials 1983, vol. 4 Oct., pp. 262–266.

(List continued on next page.)

*Primary Examiner*—Edward J. Webman
(74) *Attorney, Agent, or Firm*—Fredrikson & Byron, PA

(57) ABSTRACT

The present invention relates to an improved method of making drug delivery devices for the controlled release of pharmacologically active agents and further, to drug delivery devices made by such method. More specifically, the present invention relates to a method of forming a film comprising one or more biodegradable polymeric materials, one or more pharmacologically active agents, and one or more biocompatible solvents. The film is then partially dried, rolled or otherwise shaped, and then compressed. In this manner, the amount of pharmacologically active agent (s) that can be incorporated into the drug delivery device is increased and the pharmacologically active agent(s) is/are substantially homogeneously distributed throughout the drug delivery device. As a result, the release characteristics of the pharmacologically active agent from the drug delivery device are enhanced.

33 Claims, 3 Drawing Sheets

OTHER PUBLICATIONS

Dickinson, et al., Biodegradation of a poly(α–amino acid) hydrogel. I. In vivo, Journal of Biomedical Materials Research, vol. 15, 577–589 (1981).

Chvapil et al., Some Chemical and Biological Characteristics of a New Collagen–Polymer* Compound Material, J. Biomed. Mater. Res. vol. 3, pp. 315–331 (1969).

Fernandes et al., Regulation of Polymeric Implants for Site–specific Drug Delivery, Polymeric Site–specific Pharmcotherapy, Chapter 16, pp. 424–441.

Masters, Improvements in Perineural Local Anesthetic Block, Abstract, CRISP—Computer Retrieval of Information on Scientific Projects, printed Sep. 22, 1998.

Masters et al., Prolonged Regional Nerve Blockade by Controlled Release of Local Anesthetic from a Biodegradable Polymer Matrix, Anesthesiology, vol. 79, No. 2, Aug. 1993, pp. 340–346.

Masters et al., Sustained Local Anesthetic Relapse from Bioerodible Polymer Matrices: A Potential Method for Prolonged Regional Anesthesia, Pharmaceutical Research, vol. 10, No. 10, 1993, pp. 1527–1532.

Davis, et al., Chemically Cross–Linked Albumin Microspheres for the Controlled Release of Incorporated Rose Bengal After Instramuscular Injection Into Rabbits, Journal of Controlled Release, 4 (1987) 293–302.

* cited by examiner

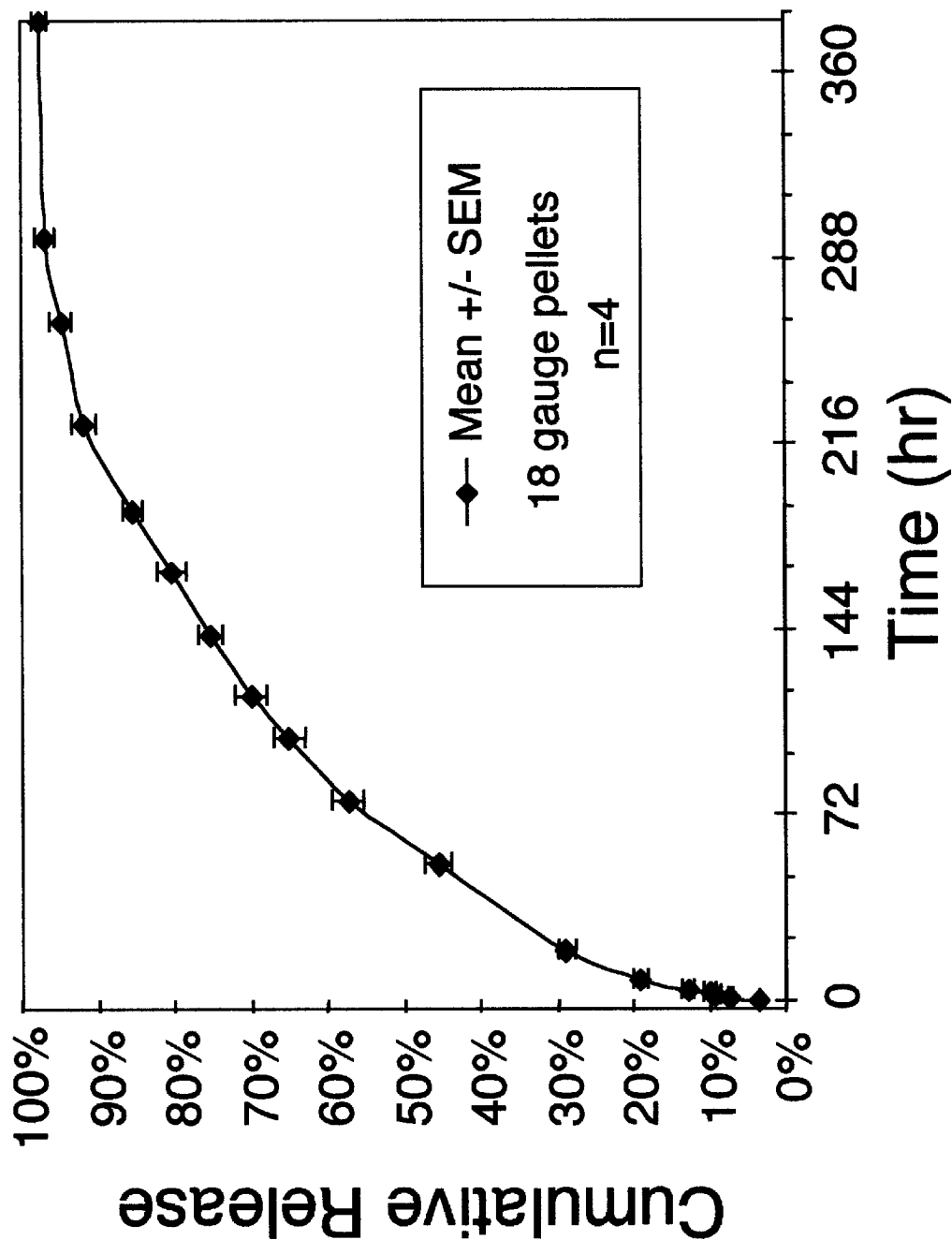

DRUG DELIVERY DEVICES COMPRISING BIODEGRADABLE PROTEIN FOR THE CONTROLLED RELEASE OF PHARMACOLOGICALLY ACTIVE AGENTS AND METHOD OF MAKING THE DRUG DELIVERY DEVICES

CROSS-REFERENCE TO RELATED APPLICATION

This application is a completion application of U.S. Provisional Application Serial No. 60/060,048, filed Sep. 25, 1997 and claims priority therefrom. U.S. Provisional Application Serial No. 60/060,048 is incorporated by reference herein.

GOVERNMENTAL RIGHTS

At least a portion of the research described in this application was supported at least in part by Governmental funding in the form of NIH Grant No. 5R10GM51917-02. The Government has certain rights in the invention.

FIELD OF THE INVENTION

The present invention relates to an improved method of making drug delivery devices for the controlled release of pharmacologically active agents and further, to drug delivery devices made by such method. More specifically, the present invention relates to a method of forming a film comprising one or more biodegradable polymeric materials, one or more pharmacologically active agents, and one or more biocompatible solvents. The film is then partially dried, rolled or otherwise shaped, and then compressed. In this manner, the amount of pharmacologically active agent(s) that can be incorporated into the drug delivery device is increased and the pharmacologically active agent(s) is/are substantially homogeneously distributed throughout the drug delivery device. As a result, the release characteristics of the pharmacologically active agent from the drug delivery device are enhanced.

BACKGROUND OF THE INVENTION

Systemic delivery, e.g., as by inhalation or ingestion, of pharmacologically active agents, although an effective and easily managed mode of administration, is less than adequate for some treatment applications. For example, some pharmacologically active agents are poorly absorbed from the blood stream, or alternatively, irritate the stomach lining. Thus, in some instances, local delivery of pharmacologically active agents is desirable.

For example, local delivery of pharmacologically active agents to peripheral nerves is often times desirable for the management of acute and chronic pain. However, local delivery of pharmacologically active agents to peripheral nerves is currently primarily performed by bolus injections or by the insertion of an infusion catheter. Although bolus injections are generally a safe and efficacious form of treatment, this mode of local delivery can be limited by the volume of liquid that can be injected, the maximal non-toxic concentration of the pharmacologically active agent that can be administered, and the system toxicity levels that can ensue subsequent to absorption and circulation to other body organs. Furthermore, inasmuch as delivery via an infusion catheter requires monitoring to initially place the catheter, and continually thereafter to ensure that the catheter does not migrate, this mode of local delivery is also suboptimal. Thus, alternative methods of localized drug delivery would be desirable.

In efforts to address this need, many implantable drug delivery devices have been developed over the past several years. Such drug delivery devices may be formulated from synthetic or natural, biodegradable or non-biodegradable, polymers. Biodegradable polymers are preferred since these materials gradually degrade in vivo over time, e.g., by enzymatic or non-enzymatic hydrolysis, when placed in an aqueous, physiological environment. Thus, the use of biodegradable polymers in drug delivery devices is preferred since their use avoids the necessary removal of the drug delivery device at the end of the release period.

Hydrogel-forming polymeric materials, in particular, have been found to be useful in the formulation of drug delivery devices. See, e.g., Lee, *J. Controlled Release*, 2, 277 (1985). Hydrogel-forming polymers are polymers that are capable of absorbing a substantial amount of water to form elastic or inelastic gels. Many non-toxic hydrogel-forming polymers are known and are easy to formulate. Furthermore, drug delivery devices incorporating hydrogel-forming polymers offer the flexibility of being capable of being implantable in liquid or gelled form. Once implanted, the hydrogel forming polymer absorbs water and swells. The release of a pharmacologically active agent incorporated into the device takes place through this gelled matrix via a diffusion mechanism.

However, many hydrogels, although biocompatible, are not biodegradable. Furthermore, most drug delivery devices comprising hydrogels require the use of undesirable organic solvents for their manufacture. Residual amounts of such solvents could potentially remain in the drug delivery device, where they could cause solvent-induced toxicity in surrounding tissues or cause structural or pharmacological degradation to the pharmacologically active agents incorporated within the drug delivery device. Finally, implanted drug delivery devices in general, and implanted drug delivery devices comprising hydrogel-forming polymers in particular, oftentimes provide suboptimal release characteristics of the drug(s) incorporated therein. That is, typically, the release of pharmacologically active agents from an implanted drug delivery device is irregular, e.g., there is an initial burst period when the drug is released primarily from the surface of the device, followed by a second period during which little or no drug is released, and a third period during which most of the remainder of the drug is released.

Thus, it would be desirable to provide improved drug delivery devices capable of sustained, controlled local delivery of pharmacologically active agents when implanted while also being biodegradable and resorbable such that removal of the device is not necessary. It would further be desirable to control the rate of delivery from such devices to avoid possible side effects associated with irregular delivery, e.g., high drug concentration induced tissue toxicity. Finally, it would be advantageous if such devices could be manufactured with biocompatible solvents so that the potential for residual solvent toxicity is reduced.

SUMMARY OF THE INVENTION

The present invention relates to an improved method of manufacturing drug delivery devices and further, to drug delivery devices made by such method. More specifically, the method of the present invention comprises combining one or more biodegradable polymeric materials, one or more pharmacologically active agents, and at least one biocompatible solvent to form a coatable composition. This composition is then coated so as to form a film (preferably a substantially planar body having opposed major surfaces and preferably having a thickness between the major surfaces of from about 0.1 millimeters to about 5 millimeters) that is subsequently at least partially dried until the film is cohesive, formed (rolled, folded, accordion-pleated, crumpled, or otherwise shaped) into a cohesive body having a surface area less than that of the film, and then compressed to provide a drug delivery device in accordance with the present invention. Drug delivery devices made utilizing the method of the present invention are capable of the sustainable, controllable local delivery of pharmacologically active agent(s), while also providing the advantage of being capable of being degraded, and preferably safely resorbed, thereby eliminating the need for the removal of the drug delivery device.

Thus, in one aspect, the present invention provides an improved method of making drug delivery devices. Specifically, the method comprises the steps of preparing a coatable composition comprising one or more biodegradable polymeric materials, one or more pharmacologically active agents, and one or more biocompatible solvents. Preferably, the biocompatible solvent is water, dimethyl sulfoxide (DMSO), ethanol, an oil, combinations of these, or the like. More preferably, the biocompatible solvent comprises water. The coatable composition is then coated to form a film and dried until the coated film can be formed into a cohesive body, e.g., preferably until the film has a solvent content of from about 50% to about 70%. The film is then formed into the cohesive body, preferably with a surface area less than that of the film. The film is then shaped into a cohesive body, e.g., rolled, folded, accordion-pleated, crumpled, or otherwise shaped into a cylinder or shaped into a ball, cube and the like, preferably with a surface area less than that of the film. The cohesive body is then compressed to remove as much of the solvent as possible so that the compressed body remains cohesive, but without removing so much solvent that the compressed body becomes brittle or otherwise lacks cohesiveness. Typically, the resulting drug delivery device has a solvent content of from about 30% to about 60%, preferably from about 40% to about 50%.

It has now been discovered that, by coating the aforementioned components into a film, partially drying the film, forming the film into a cohesive body and subsequently compressing the cohesive body, that a drug delivery device is provided with a substantially homogeneous distribution of the pharmacologically active agent(s). Due to this substantially homogeneous distribution and also to the fact that the device degrades over time, the drug delivery device of the present invention provides a sustainable and controllable release of the pharmacologically active agent(s). Furthermore, the method of the present invention utilizes biodegradable, and preferably resorbable, polymeric materials. As a result, a drug delivery device formed in accordance with the method of the present invention does not have to be removed once inserted or implanted. Finally, the method of the present invention utilizes biocompatible solvents. As such, any solvent remaining in the drug delivery device after the manufacture thereof presents a reduced, if not substantially eliminated, risk of producing undesirable side effects when implanted into a patient.

Thus, in another aspect, the present invention provides a drug delivery device made in accordance with the method of the present invention. Preferably, the biodegradable polymeric material incorporated into a device in accordance with the present invention comprises a biodegradable protein, more preferably, a water-absorbing, biodegradable protein, most preferably, a genetically engineered, water-absorbing, biodegradable protein comprising silklike blocks and elastinlike blocks. The drug delivery device can incorporate any desired pharmacologically active agent or even a second drug delivery device, e.g., corticosteroids, opioid analgesics, neurotoxins, local anesthetics, vesicles, liposheres, microspheres, enzymes, combinations of these, and the like.

It has now additionally been discovered that the sustainable release and rate controllable characteristics of the present drug delivery device may also been beneficially utilized to deliver other drug delivery devices that are either vulnerable to migration from the delivery site and/or are potentially undesirably reactive with surrounding bodily fluids or tissues. That is, not only can the drug delivery device of the present invention be beneficially utilized to deliver a pharmacologically active agent to a particular site where a therapeutic effect is desired, but also the drug delivery device of the present invention may be a "two-stage drug delivery device" utilized to deliver a second, migration-vulnerable drug delivery device comprising a pharmacologically active agent so that the second, migration-vulnerable and/or reactive drug delivery device is held in place, e.g., by the gelled matrix provided by the drug delivery device of the present invention. In the instance that the two-stage drug delivery device is used to deliver a reactive drug delivery device, the gelled matrix of the two stage drug delivery device reduces, if not substantially prevents the second drug delivery device from undesirably reacting with surrounding bodily tissues and/or fluids.

Thus, in another aspect, the present invention provides a drug delivery device comprising a compressed matrix comprising at least one biodegradable polymeric material and at least one such substance vulnerable to migration and/or reaction with surrounding tissues or bodily fluids, wherein said substance is substantially homogeneously distributed within the matrix. Examples of such substances include, but are not limited to, vesicles, such as liposheres or liposomes, comprising an encapsulated pharmacologically active agent, microspheres comprising an encapsulated pharmacologically active agent, combinations of these, and the like.

Inasmuch as the drug delivery devices of the present invention provide the sustained release of pharmacologically active agents in a rate controllable fashion, are capable of delivering other migration-vulnerable and/or reactive drug delivery devices and furthermore are produced in a manner that reduces, if not eliminates, the risk of residual solvent toxicity, there is also provided in accordance with the present invention a method of effecting a local therapeutic response in a patient in need of such treatment. Specifically, the method comprises the step of delivering a drug delivery device in accordance with the present invention to the site at which a local therapeutic response is desired. Preferably, the therapeutic response effected is an analgesic response, an antiinflammatory response, an anesthetic response, a response preventative of an immunogenic response, combinations of these, and the like.

As used herein, unless stated otherwise, all percentages are percentages based upon the weight of the biodegradable polymeric material.

BRIEF DESCRIPTION OF THE FIGURES

The above mentioned and other advantages of the present invention, and the manner of attaining them, will become more apparent and the invention itself will be better understood by reference to the following description of the embodiments of the invention taken in conjunction with the accompanying drawing, wherein:

FIG. 4 is a graphical illustration of the in vitro release characteristics of the pharmacologically active agent, sufentanil, from a drug delivery device in accordance with the present invention.

DETAILED DESCRIPTION OF THE PRESENTLY PREFERRED EMBODIMENTS

Figure 1:
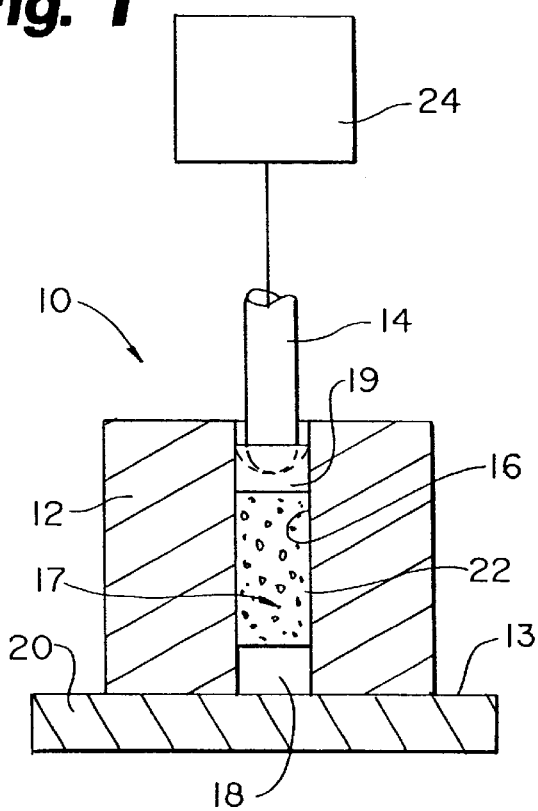
FIG. 1 is a schematic illustration, in partial cross-sectional view, of a compression molding device that may be used in the method of the present invention in a configuration prior to compression.

The embodiments of the invention described below are not intended to be exhaustive or to limit the invention to the precise forms disclosed in the following detailed description. Rather, the embodiments are chosen and described so that others skilled in the art may appreciate and understand the principles and practices of the present invention.

The present invention relates to an improved method of making a drug delivery device and further, to drug delivery devices made by said method. More specifically, the method of the present invention involves preparing a coatable composition comprising one or more biodegradable polymeric materials, one or more pharmacologically active agents and one or more biocompatible solvents. The coatable composition is then coated to form a film that is subsequently partially dried, formed into a cohesive body, and then compressed to provide a drug delivery device in accordance with the present invention.

While not wishing to be bound by any theory, it is believed that, by preparing a coatable composition from the aforementioned components, coating this composition to form a film that is subsequently partially dried, and then forming the film into a cohesive body, a relatively homogeneous distribution of the components is obtained in the cohesive body. Furthermore, when the film has dried enough so as to be cohesive unto itself, e.g., to a solvent content from about 50% to about 70%, subsequently formed into a cohesive body and then compressed, many, if not all, of any distribution anomalies are removed or resolved so that the distribution of the pharmacologically active agent is rendered substantially homogenous throughout the resulting drug delivery device.

Furthermore, the resulting drug delivery device preferably has as little solvent as possible while still being cohesive, e.g., preferably a solvent content of from about 30% to about 60%, more preferably a solvent content of from about 40% to about 50%. It is believed that, by partially drying the film to form a cohesive body and subsequently compressing the cohesive body, thereby forcing more solvent out of the body, that the resulting drug delivery device may have a significantly higher concentration of pharmacologically active agent relative to other components of the device than is obtainable in drug delivery devices produced by other methods. As a result of the substantially uniform dispersion of a greater concentration of pharmacologically active agent, a sustained, controlled release of the pharmacologically active agent is achieved, while avoiding the initial high concentration effects that can be associated with other drug delivery devices or bolus injections of pharmacologically active agents.

Reducing the solvent content has the additional effect that the resulting drug delivery device is hard, handleable, and thus, easy to insert or implant. However, upon insertion, the polymeric material of the drug delivery device absorbs water and swells to form a gelled matrix that holds the drug delivery device substantially in the desired location and also biodegrades and resorbs over time.

To form the coatable composition, the biodegradable polymeric material(s), the pharmacologically active agent (s), and the biocompatible solvent(s) may be combined in any manner. For example, the components may simply be combined in one step, or alternatively, the biodegradable polymeric material may be dissolved and/or suspended in a biocompatible solvent and the pharmacologically active agent dissolved and/or suspended in the same or another biocompatible solvent and then the resulting two solutions mixed.

Once prepared, the coatable composition may be coated onto any suitable surface from which it may be released after drying by any suitable method. Examples of suitable coating techniques include spin coating, gravure coating, flow coating, spray coating, coating with a brush or roller, screen printing, knife coating, curtain coating, slide curtain coating, extrusion, squeegee coating, and the like. The coated film (preferably having a substantially planar body having opposed major surfaces) is desirably thin enough so as to be capable of drying within a reasonable amount of time and also thin enough so that the film can be formed into a cohesive body comprising a substantially homogeneous dispersion of the components of the coatable composition. For example, a thinner film will tend to form a more homogeneous cohesive body when the film is formed into the shape of a cylinder. A typical coated film of the coatable composition have a thickness in the range of from about 0.01 millimeters to about 5 millimeters, more preferably from about 0.05 millimeters to about 2 millimeters.

Initially, when the film is first coated, it is likely to be non-cohesive, fluidly flowable, and/or non self-supporting. Thus, the coated film is preferably dried sufficiently so that it becomes cohesive, i.e., the film preferably sticks to itself rather than other materials. The film may simply be allowed to dry at room temperature, or alternatively, may be dried under vacuum, conditions of mild heating, i.e., heating to a temperature of from about 25° C. to about 50° C., or conditions of mild cooling, i.e. cooling to a temperature of from about 0° C. to about 10° C. When utilizing heat to dry the film, care should be taken to avoid denaturation or structural degradation of the pharmacologically active agent incorporated therein.

The specific solvent content at which the film becomes cohesive unto itself will depend on the individual components incorporated into the coatable composition. Generally, films that have too high of a solvent content will not be cohesive. Films that have too low of a solvent content will tend to crack, shatter, or otherwise break apart upon efforts to form them into a cohesive body. With these considerations in mind the solvent content of a partially dried film will preferably be from about 40% to about 80%, more preferably from about 50% to about 70%.

Once the film is capable of forming a cohesive body, such a cohesive body may be formed by any of a number of methods. For example, the film may be rolled, folded, accordion-pleated, crumpled, or otherwise shaped such that the resulting cohesive body has a surface area that is less than that of the coated film. For example the film can be shaped into a cylinder, a cube, a sphere or the like.

Preferably, the cohesive body is formed by rolling the coated film to form a cylinder, since the resulting cylindrical drug delivery device can be cross cut to form a plurality of virtually identical wafer-shaped drug delivery devices.

Once so formed, the cohesive body is compressed to form a drug delivery device in accordance with the present invention. Any manually or automatically operable mechanical, pneumatic, hydraulic, or electrical molding device capable of subjecting the cohesive body to pressure is suitable for use in the method of the present invention. Preferably, such a molding device is capable of applying a pressure of from about 100 pounds per square inch (psi) to about 30,000 psi for a time period of from about 10 seconds to about 48 hours. More preferably, the molding device used in the method of the present invention will be capable of applying a pressure of from about 1000 psi to about 4000 psi for a time period of from about 1 minute to about 60 minutes.

Compression molding devices suitable for use in the practice of the method of the present invention are generally known. Suitable devices may be manufactured by a number of vendors according to provided specifications, such as desirable pressure, desired materials for formulation, desired pressure source, desired size of the moldable and resulting molded device, and the like. For example, Gamir Engineering, located in Mississauga, Ontario manufactures compression molding devices to specifications provided by the customer. Additionally, many compression molding devices are commercially available.

A compression molding device 10 suitable for use in the method of the present invention is schematically shown in FIG. 1. Compression molding device 10 is equipped with a mold body 12 in which cohesive body 22 can be subjected to pressure in order to compress and mold the cohesive body 22 into a drug delivery device in accordance with the present invention. Mold body 12 is shown supported in position on a base plate 20. More specifically, mold body 12 has provided therein a cavity 16 that preferably extends all the way through mold body 12. Within the cavity 16 a molding chamber 17 can be defined into which a cohesive body in accordance with the present invention may be inserted. The cavity 16 may comprise a bore of any shape that may be machined, formed, cast or otherwise provided into the mold body 12. An inner insert 18 is preferably slidably fit within cavity 16 to be positioned against one surface 13 of the base plate 20 to define the molding chamber 17 and support to cohesive body 22 when positioned within the molding chamber 17. The insert 18 is thus fixed with respect to the mold body 12 to define the inner extent of the molding chamber 17. An outer insert 19 is also preferably provided to be slidable within the cavity 16.

Outer insert 19 is used to close the molding chamber 17 of cavity 16 after the inner insert 18 and the cohesive body 22 are provided in that order within the cavity 16. The inner and outer inserts 18 and 19, respectively, can be the same or different from one another, but both are preferably slidably movable within the cavity 16. Most preferably, the inserts 18 and 19 are shaped similarly to the shape of the cavity 16 to slide therein and are sized to effectively prevent the material of the cohesive body 22 to pass between the inserts 18 and 19 and the walls of cavity 16 when the cohesive body 22 is compressed as described below. However, the sizing is preferably such that moisture can escape between one or both inserts 18 and 19 from the cohesive body 22 during compression. Otherwise, other conventional or developed means can be provided to permit moisture to escape from the mold cavity during compression. For example, small openings could pass through one or both of the inserts 18 and 19 or mold body 12 which may also include one-way valve devices. Insert 18 may be eliminated so that surface 13 of base plate 20 defines the lower constraint to molding chamber 17. However, the use of insert 18 is beneficial, in that its presence facilitates easy removal of the cohesive body 22 after compression (described below) and provides a sufficiently hard surface against which the cohesive body 22 can be compressed. Moreover, by utilizing a series of differently sized and/or shaped inner inserts 18, the volume of the molding chamber can be varied, or different end features may be provided to the cohesive body 22. Outer inserts 19 can likewise be varied.

Outer insert 19 is also positioned to be advanced within cavity 16 or retracted from cavity 16 by a plunger 14. Preferably, the contacting surfaces of outer insert 19 and plunger 14 provide a cooperating alignment structure so that pressure can be evenly applied to the cohesive body 22. The plunger 14 may comprise a part of, or may be operatively connected with a pressure generation mechanism 24 that has the ability to apply pressure of the type and force necessary to achieve the results of the present invention. Conventional or developed technologies are contemplated, such as using mechanical, hydraulic, pneumatic, electrical, or other systems. Such systems can be manually or automatically operable.

Plunger 14 operates independently of mold body 12 and is operationally coupled to the pressure generation mechanism 24. Pressure generation mechanism 24 may be any pressure source capable of applying from about 100 psi to about 30000 psi for a time period of from about 10 seconds to about 48 hours, preferably capable of applying from about 1000 psi to about 4000 psi for a time period of from about 1 minute to about 60 minutes. Preferably, plunger 14 is formulated of a material capable of translating substantially all of the pressure applied by pressure generation mechanism 24 to cohesive body 22.

Mold body 12 may be fabricated from any material capable of withstanding the pressure to be applied from pressure generation mechanism 24, e.g., high density polyethylene, Teflon®, steel, stainless steel, titanium, brass, copper, combinations of these and the like. Desirably, mold body 12 is fabricated from a material that provides low surface friction to inserts 18 and 19 and cohesive body 22. Alternatively, surfaces defining the cavity 16 may be coated with a low friction material, e.g., Teflon®, to provide such low surface friction. Due to its relatively low cost, sufficient strength and surface friction characteristics, mold body 12 is desirably fabricated from brass. Cavity 16, extending substantially through mold body 12, may be of any shape and configuration, as determined by the desired configuration of the resulting, compressed drug delivery devices. Desirably, cavity 16 is cylindrical. As above, inserts 18 and 19 preferably fit within cavity 16 in a manner that allows moisture to escape from mold body 12, and so that inserts 18 and 19 may be easily inserted into and removed from cavity 16. Furthermore, it is preferred that inserts 18 and 19 fit within cavity 16 in a manner that provides adequate support and containment for cohesive body 22, so that, upon compression, the material of cohesive body 22 does not escape cavity 16 in a manner that would produce irregularly shaped edges on the resulting drug delivery device.

Figure 2:
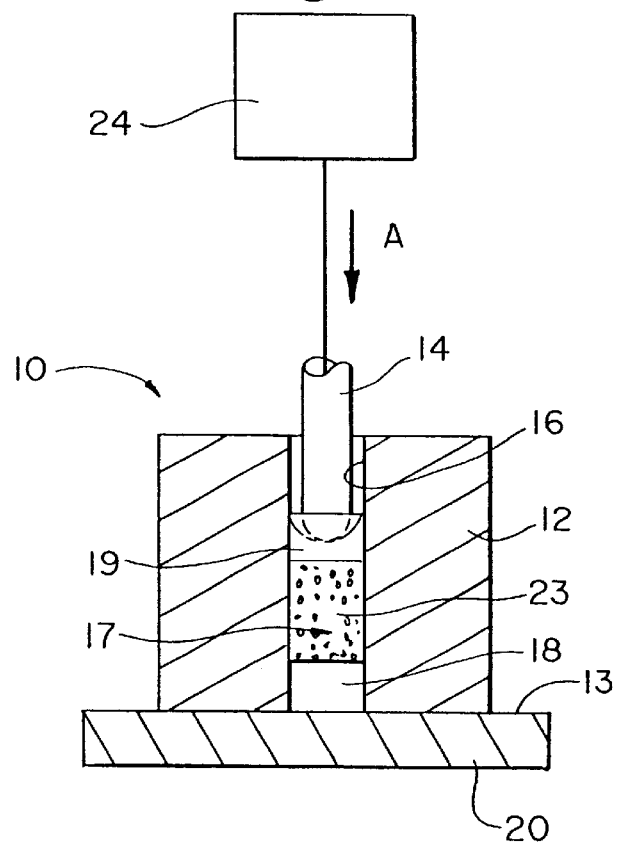
FIG. 2 is a schematic illustration, in partial cross-sectional view, of a compression molding device that may be used in the method of the present invention in a configuration during compression.

According to one procedure for using compression molding device 10 to carry out the method of the present invention, the mold body 12 is positioned as shown in FIG. 1 on the base plate 20, which itself may be supported in any manner. Then, an inner insert 18 is placed into cavity 16 followed by a cohesive body 22 to be compressed and an outer insert 19 as shown. Plunger 14 is then positioned so as to be in driving engagement with outer insert 19. Then, as schematically illustrated in FIG. 2, the pressure generation mechanism 24 is activated to move plunger 14 in the direction of arrow A to reduce the volume of the molding cavity 17 to make a compressed cohesive body 23. Pressure generation mechanism 24 applies sufficient pressure, i.e., from about 100 psi to about 30,000 psi for a time period of from about 10 seconds to about 48 hours, to plunger 14, insert 19 and cohesive body 22 against the inner insert 18, thereby driving moisture from and compressing cohesive body 22 into a drug delivery device in accordance with the present invention.

Figure 3:
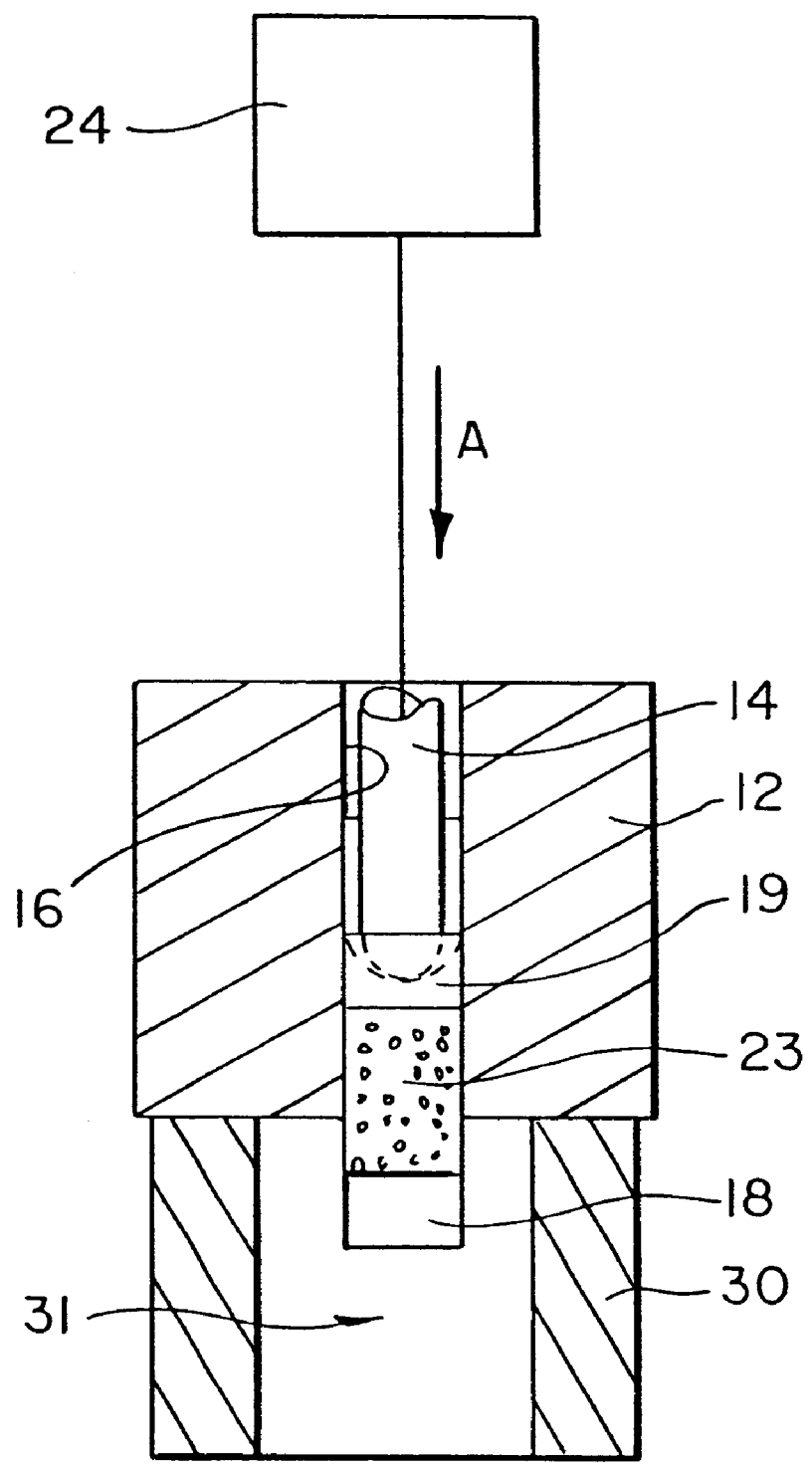
FIG. 3 is a schematic illustration, in partial cross-sectional view, of a compression molding device that may be used in the method of the present invention in a configuration during ejection.

As shown in FIG. 3, the compressed cohesive body 23 can then be ejected from the mold body 12 along with inserts 18 and 19 by positioning the mold body 12 on a support spacer 30 and further advancing the plunger 14 in the direction of arrow A by the pressure generation mechanism 24. Base plate 20 is not sued in the ejection configuration. The support spacer 30 is preferably shaped and dimensioned to provide an open volume 31 for the compressed cohesive body 23 to be easily removed. That is, when the plunger 14 is sufficiently advanced, the insert 18 and compressed cohesive body 23 can fall into the open volume 31 within the support spacer 30. After completion, the plunger 14 can be fully retracted so that the compression molding device 10 can be reconfigured for a next operation.

Any biodegradable polymeric material may be utilized in the method and corresponding drug delivery device of the present invention. Preferably, any such material will at least be water-compatible, and more preferably will be water-absorbing or hydrogel forming. Furthermore, one or more biodegradable polymeric materials may be incorporated into the drug delivery device of the present invention and may desirably be selected based upon their degradation properties to alter the release characteristics, or duration of the pharmacologically active agent. For example, two polymeric materials, and in particular, one polymeric material that degrades slowly relative to another, may be incorporated into the drug delivery device in order to provide controllable release of the pharmacologically active agent incorporated into the drug delivery device. That is, while the relatively fast-degrading polymeric material will degrade quickly thereby releasing drug relatively quickly upon insertion or implantation, such degradation will leave behind a matrix of slow-degrading polymeric material that will release the remaining pharmacologically active agent(s) over a longer period of time. Examples of biodegradable polymeric materials suitable for use in the drug delivery device of the present invention include, but are not limited to, a polypeptide, polyethylene oxide, polyethylene glycol, polylactic acid, polyglycolic acid, polypropylene oxide, poly(akylene)glycol, polyoxyethylene, sebacic acid, 1,3-bis (carboxyphenoxy)propane, copolymers of these, and the like.

In preferred embodiments, the biodegradable polymeric material comprises a biodegradable protein. More preferably, the biodegradable polymeric material comprises a water-absorbing, biodegradable protein. The utilization of a water-absorbing biodegradable protein provides the advantage that, not only will the resulting drug delivery device be biodegradable, but also resorbable. That is, that the metabolites of the degradation of the water-absorbing biodegradable protein may be reused by the patient's body rather than excreted. The biodegradable protein utilized may either be naturally occurring, e.g., such as elastin, or genetically engineered. Inasmuch as heterogeneity in molecular weight, sequence and stereochemistry can influence the function of a protein in a drug delivery device, genetically engineered proteins are preferred in that a higher degree of control can be exercised over these parameters.

One specific example of a particularly preferred genetically engineered protein for use in the drug delivery device of the present invention is that commercially available under the nomenclature "SELP" from Protein Polymer Technologies, Inc. San Diego, Calif. SELP's are a family of genetically engineered protein polymers consisting of silk-like and elastinlike blocks in various block lengths and compositional ratios. The nature of the elastinlike blocks, and their length and position within the monomers influences the water solubility of the SELP polymers. For example, decreasing the length and/or content of the silklike block domains, while maintaining the length of the elastin-like block domains, increases the water solubility of the polymers. For a more detailed discussion of the production of SELP's as well as their properties and characteristics see, for example, in J. Cappello et al., *Biotechol. Prog.*, 6, 198 (1990), the full disclosure of which is incorporated by reference herein. One preferred SELP, SELP7, has an elastin:silk ratio of 1.33, and has 45% silklike protein material and is believed to have weight average molecular weight of 80,338.

The amount of the biodegradable polymeric component utilized in the coatable composition will be dependent upon the amount of coatable composition desired and the particular biodegradable polymeric component chosen for use in the coatable composition, as the amount of coatable composition utilized in the coating of the film will be determinative of the size of the film, and thus, the size of the cohesive body and the resulting drug delivery device. That is, inasmuch as the amounts of the remaining components are dependent upon the amount of biodegradable polymeric component utilized, the amount of biodegradable polymeric component may be chosen based upon the aforementioned parameters.

Any biocompatible solvent may be utilized in the method and corresponding drug delivery device of the present invention. By using a biocompatible solvent, the risk of adverse tissue reactions to residual solvent remaining in the device after manufacture is minimized. Additionally, the use of a biocompatible solvent reduces the potential structural and/or pharmacological degradation of the pharmacologically active agent that some such pharmacologically active agents undergo when exposed to organic solvents.

Suitable biocompatible solvents for use in the method of the present invention include, but are not limited to, water; dimethyl sulfoxide (DMSO); ethanol; oils, such as olive oil, peanut oil and the like; combinations of these and the like. Preferably, the biocompatible solvent comprises water. The amount of biocompatible solvent utilized in the coatable composition will preferably be that amount sufficient to result in the composition being fluid and flowable enough to be coatable. Generally, the amount of biocompatible solvent suitable for use in the method of the present invention will range from about 50% to about 300%, preferably from about 100% to about 200% by weight, based upon the weight of the biodegradable polymeric material.

In addition to the biodegradable polymeric material(s) and the biocompatible solvent(s), the drug delivery device of the present invention comprises one or more pharmacologically active agents. As used herein, "pharinacologically active agent" generally refers to a pharmacologically active agent having a direct or indirect beneficial therapeutic effect upon introduction into a host. The phrase "pharmacologically active agent" is also meant to indicate prodrug forms thereof. A "prodrug form" of a pharmacologically active agent means a structurally related compound or derivative of the pharmacologically active agent which, when administered to a host is converted into the desired pharmacologically active agent. A prodrug form may have little or none of the desired pharmacological activity exhibited by the pharmacologically active agent to which it is converted.

Representative examples of pharmacologically active agents that may be suitable for use in the drug delivery device of the present invention include (grouped by therapeutic class):

Antidiarrhoeals such as diphenoxylate, loperamide and hyoscyamine;

Antihypertensives such as hydralazine, minoxidil, captopril, enalapril, clonidine, prazosin, debrisoquine, diazoxide, guanethidine, methyldopa, reserpine, trimethaphan;

Calcium channel blockers such as diltiazem, felodipine, amlodipine, nitrendipine, nifedipine and verapamil;

Antiarrhythmics such as amiodarone, flecainide, disopyramide, procainamide, mexiletene and quinidine;

Antiangina agents such as glyceryl trinitrate, erythrityl tetranitrate, pentaerythritol tetranitrate, mannitol hexanitrate, perhexilene, isosorbide dinitrate and nicorandil;

Beta-adrenergic blocking agents such as alprenolol, atenolol, bupranolol, carteolol, labetalol, metoprolol, nadolol, nadoxolol, oxprenolol, pindolol, propranolol, sotalol, timolol and timolol maleate;

Cardiotonic glycosides such as digoxin and other cardiac glycosides and theophylline derivatives;

Adrenergic stimulants such as adrenaline, ephedrine, fenoterol, isoprenaline, orciprenaline, rimeterol, salbutamol, salmeterol, terbutaline, dobutamine, phenylephrine, phenylpropanolamine, pseudoephedrine and dopamine;

Vasodilators such as cyclandelate, isoxsuprine, papaverine, dipyrimadole, isosorbide dinitrate, phentolamine, nicotinyl alcohol, co-dergocrine, nicotinic acid, glyceryl trinitrate, pentaerythritol tetranitrate and xanthinol;

Antimigraine preparations such as ergotamine, dihydroergotamine, methysergide, pizotifen and sumatriptan;

Anticoagulants and thrombolytic agents such as warfarin, dicoumarol, low molecular weight heparins such as enoxaparin, streptokinase and its active derivatives;

Hemostatic agents such as aprotinin, tranexamic acid and protamine;

Analgesics and antipyretics including the opioid analgesics such as buprenorphine, dextromoramide, dextropropoxyphene, fentanyl, alfentanil, sufentanil, hydromorphone, methadone, morphine, oxycodone, papaveretum, pentazocine, pethidine, phenoperidine, codeine dihydrocodeine, acetylsalicylic acid (aspirin), paracetamol, and phenazone;

Neurotoxins such as capsaicin;

Hypnotics and sedatives such as the barbiturates amylobarbitone, butobarbitone and pentobarbitone and other hypnotics and sedatives such as chloral hydrate, chlormethiazole, hydroxyzine and meprobamate;

Antianxiety agents such as the benzodiazepines alprazolam, bromazepam, chlordiazepoxide, clobazam, chlorazepate, diazepam, flunitrazepam, flurazepam, lorazepam, nitrazepam, oxazepam, temazepam and triazolam;

Neuroleptic and antipsychotic drugs such as the phenothiazines, chlorpromazine, fluphenazine, pericyazine, perphenazine, promazine, thiopropazate, thioridazine, trifluoperazine; and butyrophenone, droperidol and haloperidol; and other antipsychotic drugs such as pimozide, thiothixene and lithium;

Antidepressants such as the tricyclic antidepressants amitryptyline, clomipramine, desipramine, dothiepin, doxepin, imipramine, nortriptyline, opipramol, protriptyline and trimipramine and the tetracyclic antidepressants such as mianserin and the monoamine oxidase inhibitors such as isocarboxazid, phenelizine, tranylcypromine and moclobemide and selective serotonin re-uptake inhibitors such as fluoxetine, paroxetine, citalopram, fluvoxamine and sertraline;

CNS stimulants such as caffeine and 3-(2-aminobutyl) indole;

Anti-alzheimer's agents such as tacrine;

Anti-Parkinson's agents such as amantadine, benserazide, carbidopa, levodopa, benztropine, biperiden, benzhexol, procyclidine and dopamine-2 agonists such as S(−)-2-(N-propyl-N-2-thienylethylamino)-5-hydroxytetralin (N-0923);

Anticonvulsants such as phenytoin, valproic acid, primidone, phenobarbitone, methylphenobarbitone and carbamazepine, ethosuximide, methsuximide, phensuximide, sulthiame and clonazepam;

Antiemetics and antinauseants such as the phenothiazines prochloperazine, thiethylperazine and 5HT-3 receptor antagonists such as ondansetron and granisetron, as well as dimenhydrinate, diphenhydramine, metoclopramide, domperidone, hyoscine, hyoscine hydrobromide, hyoscine hydrochloride, clebopride and bromopride;

Non-steroidal anti-inflammatory agents including their racemic mixtures or individual enantiomers where applicable, preferably which can be formulated in combination with dermal penetration enhancers, such as ibuprofen, flurbiprofen, ketoprofen, aclofenac, diclofenac, aloxiprin, aproxen, aspirin, diflunisal, fenoprofen, indomethacin, mefenamic acid, naproxen, phenylbutazone, piroxicam, salicylamide, salicylic acid, sulindac, desoxysulindac, tenoxicam, tramadol, ketoralac, flufenisal, salsalate, triethanolamine salicylate, aminopyrine, antipyrine, oxyphenbutazone, apazone, cintazone, flufenamic acid, clonixeril, clonixin, meclofenamic acid, flunixin, coichicine, demecolcine, allopurinol, oxypurinol, benzydamine hydrochloride, dimefadane, indoxole, intrazole, mimbane hydrochloride, paranylene hydrochloride, tetrydamine, benzindopyrine hydrochloride, fluprofen, ibufenac, naproxol, fenbufen, cinchophen, diflumidone sodium, fenamole, flutiazin, metazamide, letimide hydrochloride, nexeridine hydrochloride, octazamide, molinazole, neocinchophen, nimazole, proxazole citrate, tesicam, tesimide, tolmetin, and triflumidate;

Antirheumatoid agents such as penicillamine, aurothioglucose, sodium aurothiomalate, methotrexate and auranofin;

Muscle relaxants such as baclofen, diazepam, cyclobenzaprine hydrochloride, dantrolene, methocarbamol, orphenadrine and quinine;

Agents used in gout and hyperuricaernia such as allopurinol, colchicine, probenecid and sulphinpyrazone;

Oestrogens such as oestradiol, oestriol, oestrone, ethinyloestradiol, mestranol, stilboestrol, dienoestrol, epioestriol, estropipate and zeranol;

Progesterone and other progestagens such as allyloestrenol, dydrgesterone, lynoestrenol, norgestrel, norethyndrel, norethisterone, norethisterone acetate, gestodene, levonorgestrel, medroxyprogesterone and megestrol;

Antiandrogens such as cyproterone acetate and danazol;

Antioestrogens such as tamoxifen and epitiostanol and the aromatase inhibitors, exemestane and 4-hydroxy-androstenedione and its derivatives;

Androgens and anabolic agents such as testosterone, methyltestosterone, clostebol acetate, drostanolone, furazabol, nandrolone oxandrolone, stanozolol, trenbolone acetate, dihydro-testosterone, 17-α-methyl-19-nortestosterone and fluoxymesterone;

5-alpha reductase inhibitors such as finasteride, turosteride, LY-191704 and MK-306;

Corticosteroids such as betamethasone, betamethasone valerate, cortisone, dexamethasone, dexamethasone 21-phosphate, fludrocortisone, flumethasone, fluocinonide, fluocinonide desonide, fluocinolone, fluocinolone acetonide, fluocortolone, halcinonide, halopredone, hydrocortisone, hydrocortisone 17-valerate, hydrocortisone 17-butyrate, hydrocortisone 21-acetate, methylprednisolone, prednisolone, prednisolone 21-phosphate, prednisone, triamcinolone, triamcinolone acetonide;

Further examples of steroidal antiinflammatory agents such as cortodoxone, fludroracetonide, fludrocortisone, difluorsone diacetate, flurandrenolone acetonide, medrysone, amcinafel, amcinafide, betamethasone and its other esters, chloroprednisone, clorcortelone, descinolone, desonide, dichlorisone, difluprednate, flucloronide, flumethasone, flunisolide, flucortolone, fluoromethalone, fluperolone, fluprednisolone, meprednisone, methylmeprednisolone, paramethasone, cortisone acetate, hydrocortisone cyclopentylpropionate, cortodoxone, flucetonide, fludrocortisone acetate, flurandrenolone acetonide, medrysone, aincinafal, amcinafide, betamethasone, betamethasone benzoate, chloroprednisone acetate, clocortolone acetate, descinolone acetonide, desoximetasone, dichlorisone acetate, difluprednate, flucloronide, flumethasone pivalate, flunisolide acetate, fluperolone acetate, fluprednisolone valerate, paramethasone acetate, prednisolamate, prednival, triamcinolone hexacetonide, cortivazol, formocortal and nivazol;

Pituitary hormones and their active derivatives or analogs such as corticotrophin, thyrotropin, follicle stimulating hormone (FSH), luteinising hormone (LH) and gonadotrophin releasing hormone (GnRH);

Hypoglycemic agents such as insulin, chlorpropamide, glibenclamide, gliclazide, glipizide, tolazamide, tolbutamide and metformin;

Thyroid hormones such as calcitonin, thyroxine and liothyronine and antithyroid agents such as carbimazole and propylthiouracil;

Other miscellaneous hormone agents such as octreotide;

Pituitary inhibitors such as bromocriptine;

Ovulation inducers such as clomiphene;

Diuretics such as the thiazides, related diuretics and loop diuretics, bendrofluazide, chlorothiazide, chlorthalidone, dopamine, cyclopenthiazide, hydrochlorothiazide, indapamide, mefruside, methycholthiazide, metolazone, quinethazone, bumetanide, ethacrynic acid and frusemide and potasium sparing diuretics, spironolactone, amiloride and triamterene;

Antidiuretics such as desmopressin, lypressin and vasopressin including their active derivatives or analogs;

Obstetric drugs including agents acting on the uterus such as ergometrine, oxytocin and gemeprost;

Prostaglandins such as alprostadil (PGE1), prostacyclin (PGI2), dinoprost (prostaglandin F2-alpha) and misoprostol;

Antimicrobials including the cephalosporins such as cephalexin, cefoxytin and cephalothin;

Penicillins such as amoxycillin, amoxycillin with clavulanic acid, ampicillin, bacampicillin, benzathine penicillin, benzylpenicillin, carbenicillin, cloxacillin, methicillin, phenethicillin, phenoxymethylpenicillin, flucloxacillin, meziocillin, piperacillin, ticarcillin and azlocillin;

Tetracyclines such as minocycline, chlortetracycline, tetracycline, demeclocycline, doxycycline, methacycline and oxytetracycline and other tetracycline-type antibiotics;

Aminoglycosides such as amikacin, gentamicin, kanamycin, neomycin, netilmicin and tobramycin;

Antifungals such as amorolfine, isoconazole, clotrimazole, econazole, miconazole, nystatin, terbinafine, bifonazole, amphotericin, griseofulvin, ketoconazole, fluconazole and flucytosine, salicylic acid, fezatione, ticlatone, tolnaftate, triacetin, zinc, pyrithione and sodium pyrithione;

Quinolones such as nalidixic acid, cinoxacin, ciprofloxacin, enoxacin and norfloxacin;

Sulphonamides such as phthalysulphthiazole, sulfadoxine, sulphadiazine, sulphamethizole and sulphamethoxazole;

Sulphones such as dapsone;

Other miscellaneous antibiotics such as chloramphenicol, clindamycin, erythromycin, erythromycin ethyl carbonate, erythromycin estolate, erythromycin glucepate, erythromycin ethylsuccinate, erythromycin lactobionate, roxithromycin, lincomycin, natamycin, nitrofurantoin, spectinomycin, vancomycin, aztreonain, colistin IV, metronidazole, tinidazole, fusidic acid, trimethoprim, and 2-thiopyridine N-oxide; halogen compounds, particularly iodine and iodine compounds such as iodine-PVP complex and diiodohydroxyquin, hexachlorophene; chlorhexidine; chloroamine compounds; and benzoylperoxide;

Antituberculosis drugs such as ethambutol, isoniazid, pyrazinamide, rifampicin and clofazimine;

Antimalarials such as primaquine, pyrimethamine, chloroquine, hydroxychloroquine, quinine, mefloquine and halofantrine;

Antiviral agents such as acyclovir and acyclovir prodrugs, famcyclovir, zidovudine, didanosine, stavudine, lamivudine, zalcitabine, saquinavir, indinavir, ritonavir, n-docosanol, tromantadine and idoxuridine;

Anthelmintics such as mebendazole, thiabendazole, niclosamide, praziquantel, pyrantel embonate and diethylcarbamazine;

Cytotoxic agents such as plicainycin, cyclophosphamide, dacarbazine, fluorouracil and its prodrugs (described, for example, in *International Journal of Pharmaceutics* 111, 223–233 (1994)), methotrexate, procarbazine, 6-mercaptopurine and mucophenolic acid;

Anorectic and weight reducing agents including dexfenfluramine. fenfluramine, diethylpropion, mazindol and phentermine;

Agents used in hypercalcaemia such as calcitriol, dihydrotachysterol and their active derivatives or analogs;

Antitussives such as ethylmorphine, dextromethorphan and pholcodine;

Expectorants such as carbolcysteine, bromhexine, emetine, quanifesin, ipecacuanha and saponins;

Decongestants such as phenylephrine, phenylpropanolamine and pseudoephedrine;

Bronchospasm relaxants such as ephedrine, fenoterol, orciprenaline, rimiterol, salbutamol, sodium cromoglycate, cromoglycic acid and its prodrugs (described, for example, in *International Journal of Pharmaceutics* 7, 63–75 (1980)), terbutaline, ipratropium bromide, salmeterol and theophylline and theophylline derivatives;

Antihistamines such as meclozine, cyclizine, chlorcyclizine, hydroxyzine, brompheniramine, chlorpheniramine, clemastine, cyproheptadine, dexchlorpheniramine, diphenhydramine, diphenylamine, doxylamine, mebhydrolin, pheniramine, tripolidine, azatadine, diphenylpyraline, methdilazine, terfenadine, astemizole, loratidine and cetirizine;

Local anaesthetics such as bupivacaine, amethocaine, lignocaine, lidocaine, cinchocaine, dibucaine, mepivacaine, prilocaine, etidocaine, veratridine (specific c-fiber blocker) and procaine;

Stratum corneum lipids, such as ceramides, cholesterol and free fatty acids, for improved skin barrier repair [Man, et al. *J. Invest. Dermatol.*, 106(5), 1096, (1996)];

Neuromuscular blocking agents such as suxamethonium, alcuronium, pancuronium, atracurium, gallamine, tubocurarine and vecuronium;

Smoking cessation agents such as nicotine, bupropion and ibogaine;

Insecticides and other pesticides which are suitable for local application;

Dermatological agents, such as vitamins A, C, $B_1$, $B_2$, $B_6$, $B_{12a}$ and E, vitamin E acetate and vitamin E sorbate;

Allergens for desensitisation such as house, dust or mite allergens;

Nutritional agents, such as vitamins, essential amino acids and fats;

Keratolytics such as the alpha-hydroxy acids, glycolic acid and salicylic acid;

The drug delivery device in accordance with the present invention, as mentioned hereinabove, may comprise an amount of a neurotoxin as the pharmacologically active agent. Specifically, inasmuch as some cases of chronic pain are the result of permanent nerve damage, in some instances it may be desirable to locally deliver an amount of a neurotoxin to the injured nerve to destroy that portion of the nerve that is the cause of the persistent, chronic pain. One example of a neurotoxin suitable for use in the present invention is capsaicin, as shown in Examples 4 and 12, hereinbelow. If a neurotoxin is to be incorporated into the drug delivery device of the present invention, it is preferred that it be incorporated in an amount ranging from about 0.001% to about 5%, more preferably, from about 0.05% to about 1% by weight, based upon the weight of the biodegradable polymeric component.

The drug delivery device of the present invention is particularly advantageous for the encapsulation/incorporation of macromolecular pharmacologically active agents such as proteins, enzymes, peptides, polysaccharides, nucleic acids, cells, tissues, and the like. Immobilization of macromolecular pharmacologically active agents into a drug delivery device can be difficult due to the ease with which some of these macromolecular agents denature when exposed to organic solvents, some constituents present in bodily fluids or to temperatures appreciably higher than room temperature. However, since the method of the present invention, as well as the drug delivery device formed by the method utilize biocompatible solvents such as water, DMSO or ethanol, and furthermore does not require heating, the risk of the denaturation of these types of materials is reduced. Furthermore, due to the size of these macromolecular pharmacologically active agents, these agents become trapped by the gelatinous mass that forms upon implantation of drug delivery devices in accordance with the present invention, and thereby are protected from constituents of bodily fluids that would otherwise denature them,. Thus, the drug delivery devices of the present invention allow these macromolecular agents may exert their therapeutic effects, while yet protecting them from denaturation or other structural degradation.

Examples of cells which can be utilized as the pharmacologically active agent in the drug delivery device of the present invention include primary cultures as well as established cell lines, including transformed cells. Examples of these include, but are not limited to pancreatic islet cells, human foreskin fibroblasts, Chinese hamster ovary cells, beta cell insulomas, lymphoblastic leukemia cells, mouse 3T3 fibroblasts, dopamine secreting ventral mesencephalon cells, neuroblastoid cells, adrenal medulla cells, T-cells combinations of these, and the like. As can be seen from this partial list, cells of all types, including dermal, neural, blood, organ, muscle, glandular, reproductive and immune system cells, as well as cells of all species of origin, can be encapsulated successfully by this method. Examples of proteins which can be incorporated into the drug delivery device of the present invention include, but are not limited to, hemoglobin, vasporessin, oxytocin, adrenocorticocotrophic hormone, epiderinal growth factor, prolactin, luliberin or luteinising hormone releasing factor, human growth factor, and the like; enzymes such as adenosine deaminase, superoxide dismutase, xanthine oxidase, and the like; enzyme systems; blood clotting factors; clot inhibitors or clot dissolving agents such as streptokinase and tissue plasminogen activator; antigens for immunization; hormones; polysaccharides such as heparin; oligonucleotides; bacteria and other microbial microorganisms including viruses; monoclonal antibodies; vitamins; cofactors; retroviruses for gene therapy, combinations of these and the like.

An efficacious amount of the aforementioned pharmacologically active agent(s) can easily be determined by those of ordinary skill in the art taking into consideration such parameters as the particular pharmacologically active agent chosen, the size and weight of the patient, the desired therapeutic effect, the pharmacokinetics of the chosen pharmacologically active agent, and the like, as well as by reference to well known resources such as Physicians' Desk Reference® PDR—52 ed (1998)—Medical Economics 1974. In consideration of these parameters, it has been found that a wide range exists in the amount of the pharmacologically active agent(s) capable of being incorporated into, and subsequently released from or alternatively allowed to exert the agent's therapeutic effects from within, the drug delivery device. More specifically, the amount of pharmacologically active agent that may be incorporated into and then either released from or active from within the drug delivery device may range from about 0.001% to about 200%, more preferably, from about 0.05% to about 100%, most preferably from about 0.1% to 70%, based on the weight of the biodegradable polymeric material.

In addition to the biodegradable polymeric material(s), the biocompatible solvent(s) and pharmacologically active agent(s), the drug delivery devices of the present invention advantageously may themselves incorporate other drug delivery devices that would otherwise typically migrate away from the desired delivery site and/or are potentially undesirably reactive with surrounding bodily fluids or tissues. Such migration is undesirable in that the therapeutic effect of the pharmacological agents encapsulated therein may occur away from the desired site, thus eliminating the advantage of localized delivery. When a drug delivery device incorporating a migration-vulnerable and/or reactive drug delivery device (hereinafter referred to as a "two-stage drug delivery device") is subsequently implanted, the migration-vulnerable and/or reactive drug delivery device(s) is/are held in place and protected by the two-stage drug delivery device. More particularly, once implanted, the biodegradable protein material of the two-stage drug delivery device will absorb water and swell thereby forming a gelatinous mass at the site of delivery. Then, as the biodegradable material of the migration-vulnerable drug delivery devices degrades, thereby releasing the pharmacologically active agents incorporated therein, the pharmacologically active agents diffuse through the gelatinous mass of the two-stage drug delivery device of the present invention. Furthermore, the gelatinous mass reduces, if not prevents, the potential for undesirable reaction with bodily fluids or tissues that may otherwise occur upon implantation of a reactive drug delivery device. Examples of such drug delivery devices subject to migration for the delivery site include, but are not limited to, vesicles, e.g., liposomes, liposheres and microspheres.

Vesicles are made up of microparticies or colloidal carriers composed of lipids, carbohydrates or synthetic polymer matrices and are commonly used in liquid drug delivery devices. Vesicles, for example, have been used to deliver anesthetics using formulations with polylactic acid, lecithin, iophendylate and phosphotidyl choline and cholesterol. For a discussion of the characteristics and efficiency of drug delivery from vesicles, see, e.g., Wakiyama et al., *Chem., Pharm. Bull.*, 30, 3719 (1982) and Haynes et al.,*Anesthiol.*, 74, 105 (1991), the entire disclosures of which are incorporated by reference herein.

Liposomes, the most widely studied type of vesicle, can be formulated to include a wide variety of compositions and structures that are potentially non-toxic, biodegradable and non-immunogenic. Furthermore, studies are in progress to create liposomes that release more drug in response to changes in their environment, including the presence of enzymes or polycations or changes in pH. For a review of the properties and charateristics of liposomes see, e.g., Langer, *Science*, 249, 1527 (1990); and Langer, *Ann. Biomed. Eng.*, 23, 101 (1995) , the entire disclosures of which are incorporated by reference herein.

Liposheres are an aqueous microdispersion of water insoluble, spherical microparticles (from about 0.2 to about 100 um in diameter), each consisting of a solid core of hydrophobic triglycerides and drug particles that are embedded with phospholipids on the surface. Liposheres are disclosed in U.S. Pat. No. 5,188,837, issued to Domb, the disclosure of which is incorporated herein by reference.

Microspheres typically comprise a biodegradable polymer matrix incorporating a drug. Microspheres can be formed by a wide variety of techniques known to those of skill in the art. Examples of microsphere forming techniques include, but are not limited to, (a) phase separation by emulsification and subsequent organic solvent evaporation (including complex emulsion methods such as oil in water emulsions, water in oil emulsions and water-oil-water emulsions); (b) coacervation-phase separation; (c) melt dispersion; (d) interfacial deposition; (e) in situ polymerization; (f) spray drying and spray congealing; (g) air suspension coating; and (h) pan and spray coating. These methods, as well as properties and characteristics of microspheres are disclosed in, e.g., U.S. Pat. No. 4,652,441; U.S. Pat. No. 5,100,669; U.S. Pat. No. 4,526,938; WO 93/24150; EPA 0258780 A2; U.S. Pat. No. 4,438,253; and U.S. Pat. 5,330,768, the entire disclosures of which are incorporated by reference herein.

Inasmuch as the migration-vulnerable and/or reactive drug delivery devices will desirably further encapsulate a pharaincologically active agent, the amount of these devices to be utilized in the two-stage drug delivery device may be determined by the dosage of the pharmacologically active agent, as determined as described hereinabove. Inasmuch as such migration-vulnerable and/or reactive drug delivery devices represent solid matter that may change the ability of the coatable composition to be coated, the amount of such devices to be included in a two-stage drug delivery device desirably ranges about 10,000 to about 1 billion, more preferably ranges from about 1 million to about 500 million, and most preferably ranges from about 200 million to about 400 million Additionally, the drug delivery devices formed according to the method of the present invention may optionally comprise one or more additives. Such additives may be utilized, for example, to facilitate the processing of the drug delivery devices, to stabilize the pharmacologically active agents, to facilitate the activity of the pharmacologically active agents, or to alter the release characteristics of the drug delivery device. For example, when the pharmacologically active agent is to be an enzyme, such as xanthine oxidase or superoxide dismutase, the drug delivery device may further comprise an amount of an enzyme substrate, such as xanthine, to facilitate the action of the enzyme. Additionally, hydrophobic substances such as lipids can be incorporated into the drug delivery device to extend the duration of drug release, while hydrophilic, polar additives, such as salts and amino acids, can be added to facilitate, i.e., shorten the duration of, drug release. Exemplary hydrophobic substances include lipids, e.g., tristearin, ethyl stearate, phosphotidycholine, polyethylene glycol (PEG); fatty acids, e.g., sebacic acid erucic acid combinations of these and the like. A particularly preferred hydrophobic additive useful to extend the release of the pharmacologically active agents comprises a combination of a dimer of erucic acid and sebacic acid, wherein the ratio of the dimer to sebacic acid is 1:4. Examplary hydrophilic additives useful to shorten the release duration of the pharmacologically active agent include but are not limited to, salts, such as sodium chloride; and amino acids, such as glutamine and glycine. If additives are to be incorporated into the coatable composition, they will preferably be included in an amount so that the desired result of the additive is exhibited. Generally, the amount of additives may vary between from about 0% to about 300%, preferably from about 100% to 200% by weight, based upon the weight of the biodegradable polymeric material.

Manufacturing drug delivery devices with the method of the present invention imparts many advantageous qualities to the resulting drug delivery devices. First of all, by compressing the cohesive body in such a manner, the resulting drug delivery device is substantially hard, i.e., with a solvent content of from about 30% to about 60%, preferably of from about 40% to about 50%. Thus, delivery of the drug delivery device is made easy, inasmuch as it may be easily handled to be injected or implanted. Furthermore, once implanted, the biodegradable polymeric material preferably will absorb water and swell, thereby forming a gelatinous matrix which helps the drug delivery device to stay substantially in the location where it was implanted or injected. Additionally, since the polymeric material is biodegradable and the pharmacologically active agent is distributed substantially homogeneously therein, the release kinetics of the pharmacologically active agent are optimized. Indeed, the components and the amounts thereof to be utilized in the drug delivery device may be selected so as to optimize the rate of delivery of the pharmacologically active agent depending upon the desired therapeutic effect and pharmacokinetics of the chosen pharmacologically active agent. Finally, since biocompatible solvents are used in the manufacture of the drug delivery devices, the potential for adverse tissue reactions to chemical solvents are reduced, if not substantially precluded.

For all of these reasons, drug delivery devices in accordance with the present invention may advantageously be used to effect a local therapeutic result in a patient in need of such treatment. More specifically, the drug delivery devices of the present invention may be injected, implanted or otherwise delivered to a site within a patient wherein such a local therapeutic effect is desired. Depending on the pharmacologically active agent utilized, the drug delivery devices may be used to produce such therapeutic effects as analgesia or anesthesia, or alternatively, may be used to treat specific conditions. Most advantageously, due to their release characteristics and biocompatibility, the drug delivery devices are utilized in instances where long term, sustained, controlled release of pharmacologically active agents is desirable, such as in the treatment of surgical and post-operative pain, cancer pain, or other conditions requiring chronic pain management.

Furthermore, the drug delivery devices of the present invention may incorporate multiple pharmacologically active agents, one or more of which may be agents that are effective to suppress an immune response. In this regard, the drug delivery devices will deter, or substantially prevent the encapsulation that typically occurs when a foreign body is introduced into a host. Such encapsulation could potentially have the undesirable effect of limiting the efficacy of the drug delivery device.

The patient to which the drug delivery device is administered may be any patient in need of such treatment. Preferably, the patient is a mammal. More preferably, the patient is a human. Furthermore, the drug delivery device can be implanted in any location to which it is desired to effect a local therapeutic response. For example, the drug delivery device may be implanted vaginally, subcutaneously, near heart valves, in periodontal pockets, in the eye, in the intracranial space, next to an injured nerve, next to the spinal cord, etc.

The present invention will now be further described with reference to the following non-limiting examples and the following materials and methods were employed.

Materials and Methods

Xanthine oxidase, superoxide dismutase, capsaicin and dexamethasone were obtained from (Sigma Chemical Company, St. Louis Mo.). The silklike, elastinlike polymer SELP7 was obtained from Protein Polymer Technologies, San Diego, Calif.

Test Method 1. Thermal Sensitivity Test.

The thermal sensitivity tests referred to hereinbelow were conducted as follows. Thermal sensitivity was measured by the time required for each rat to withdraw its hind paw from a 56° C. hot plate (commercially available under the trade designation 35-D from IITC Life Science Instruments, Woodland Hills Calif.). Specifically the rats were positioned to stand with one hind paw on a hot plate and the other on a room temperature board. Latency to withdraw each hind paw from the hot plate was recorded by alternating paws and allowing at least 15 seconds of recovery between each measurement. If no withdrawal occurred from the hot plate within 15 seconds, the trial was terminated to prevent injury and the termination time was recorded. Testing ended after three measurements per side and the mean was calculated for each side.

Test Method 2. Motor Capacity Test.

The motor capacity tests referred to hereinbelow were conducted as follows. The rat is held in the same manner as during the thermal sensitivity testing so that it is positioned to stand on one leg against an electronic balance. The resistance of the rat's leg is measured as the force against the balance in grams. Previous results from control experiments show that a 200–275 grain rat exerts about 150–225 grams of force with a normal leg. However, if the leg is showing a lack of motor capacity from local anesthetic action, then forces of only from about 30 to about 70 grams are expected. Thus, a lack of motor capacity resulting in the rat exerting only from about 30 to about 70 grams of force against the balance shows that the administered drug delivery device has delivered enough of a pharmacologically active agent to produce local anesthetic action.

EXAMPLE 1

Preparation of a Drug Delivery Device Comprising a Biodegradable Protein and an Enzyme The enzyme xanthine oxidase was dissolved in deionized water to 0.28 units/100 $\mu$l. This xanthine oxidase solution was mixed in with 50 mg protein (SELP 7) to form a coatable composition. The composition was then coated on a glass surface to form a film with a thickness of from about 0.1 to about 0.3 mm. The coated film was allowed to dry at room temperature until dry enough so as to be cohesive, i.e., to a solvent content of from about 50% to about 70%. The resulting film was rolled up, placed in a 3.5 mm diameter mold and compressed at 1750 psi for 2 minutes to form a 3.5 mm diameter cylinder, approximately 5 mm long, utilizing the compression molding device discussed hereinabove. The resulting cylinder had a solvent content of approximately 30% to about 60%. This cylinder was cut into four equal pieces so that each piece contained approximately 0.07 xanthine oxidase units/piece. These pieces were frozen at −80° C. until used within 4 weeks.

EXAMPLE 2

Preparation of a Drug Delivery Device Comprising a Biodegradable Protein and an Enzyme The enzyme superoxide dismutase (SOD) was dissolved in deionized water to 30.0 units/100 $\mu$l. This SOD solution was mixed with 50 mg (SELP7) to form a coatable composition. The composition was then coated on a glass surface to form a film with a thickness of from about 0.1 mm to about 0.3 mm. The coated film was allowed to dry at room temperature until dry enough so as to be cohesive, i.e., to a solvent content of from about 50% to about 70%. The resulting film was rolled up, placed in a 3.5 mm diameter mold and compressed at 1750 psi for 2 minutes to form a 3.5 mm diameter cylinder, approximately 5 mm long, utilizing the compression molding device discussed hereinabove. The resulting cylinder had a solvent content of from about 30% to about 60%. This cylinder was cut into four equal pieces so that each piece contained approximately 7.5 units of SOD per/piece. These pieces were frozen at −80° C. until used within 4 weeks.

EXAMPLE 3

Preparation of a Drug Delivery Device Comprising a Biodegradable Protein and Lipospheres Lipospheres with 3.6% of the local anesthetic bupivacaine were made as described in U.S. Pat. No. 5,188,837. From about 200 million to about 400 million of these lipospheres were then suspended in 150 μl deionized water. This suspension was then mixed with 30 mg SELP7 to form a coatable composition. The composition was then coated onto a glass surface to form a film with a thickness of from about 0.1 to about 0.3 mm. The coated film was allowed to dry at room temperature until the film was dry enough so as to be cohesive, i.e., to a solvent content of from about 50% to about 70%. The resulting film was rolled up, placed in a 3.5 mm diameter mold and compressed at 1750 psi for 2 minutes to form a 3.5 mm diameter cylinder, approximately 4 mm long, utilizing the compression molding device discussed hereinabove. The resulting cylinder had a solvent content of from about 30% to about 50%. Four cylinders were made according to this procedure. These cylinders were refrigerated at 4° C. until used within 4 weeks.

EXAMPLE 4

Preparation of a Drug Delivery Device Comprising a Biodegradable Protein and Two Pharmacologicaliy Active Agents Drug delivery devices were prepared with differing concentrations of the two pharmacologically active agents capsaicin and dexamethasone as follows. Specifically, first drug delivery devices were prepared comprising 6 mg of capsaicin and 6 mg dexamethasone by dissolving these amounts in 100 μl ethanol. This solution was then added to a solution of 128 mg SELP7 dissolved in 150 μl water to form a coatable composition. This composition was then coated onto a glass surface to form a film with a thickness of from about 0.1 mm to about 0.3 mm film. The coated film was allowed to dry at room temperature until dry enough so as to be cohesive, i.e., to a solvent content of from about 50% to about 70%. The resulting film was rolled up, placed in a 3.5 mm diameter mold and compressed at 7600 psi overnight to form a 3.5 mm diameter cylinder, approximately 5 mm long, utilizing the compression molding device discussed. The cylinder was dried to a solvent content of from about 30% to about 50% in a vacuum and then cut into three equal pieces. From initially added quantities, each pellet was calculated to contain approximately 2 mg capsaicin and 2 mg dexamethasone, weighing approximately 35 mg each.

Second drug delivery devices were prepared comprising 6 mg of capsaicin and 1.2 mg dexamethasone by dissolving these amounts of these agents in 25 μl ethanol. This solution was then added to a solution of 120 mg SELP7 dissolved in 200 μl deionized water to form a coatable composition. This composition was then coated onto two glass surfaces to form two films with thicknesses of from about 0.1 mm to about 0.3 mm. The films were allowed to dry at room temperature until dry enough so as to be cohesive, i.e., to a solvent content of from about 50% to about 70%. The resulting films were rolled up, each placed in a 3.5 mm diameter mold and compressed at 7600 psi overnight to form two 3.5 mm diameter cylinders, approximately 5 mm long, utilizing the compression molding device discussed. The resulting cylinders had a solvent content of from about 30% to about 60%. These cylinders were cut into 5 equal pellets. From initially added quantities, each pellet was calculated to contain approximately 2.4 mg capsaicin and 0.24 mg dexamethasone, weighing approximately 30 mg each.

EXAMPLE 5

Preparation of an Injectable Drug Delivery Device Comprising a Biodegradable Protein, an Additive and an Opioid Analgesic Injectable drug delivery devices comprising a biodegradable protein, an additive and an analgesic were made as follows. The opioid analgesic, sufentanil citrate (obtained from National Institute on Drug Abuse) was desalted by adding ammonium hydroxide and extracted with n-hexane, collection of solvent and evaporation. The desalted sufentanil was reconstituted in 20 μl of 90% ethanol containing approximately 4,500,000 cpm of tritiated sufentanil (obtained from Jannsen Pharmaceutica, Belgium) to 2.0 mg/20 μl. The biodegradable protein SELP7 was dissolved in deionized water to 20 mg SELP7/30 μl and spread into a thin layer approximately 5 cm by 5 cm in area. Immediately thereafter, 10 mg of finely pulverized powder of an additive, fatty acid dimer:sabacic acid (FAD:SA in 1:4 ratio), was added to the center of the protein solution area. Immediately thereafter, the sufentanil dissolved in the ethanol was added very slowly to the mound of FAD:SA over a time period of a few minutes, i.e., from about 1 to about 5 minutes. After the sufentanil solution had soaked into the FAD:SA powder, the components were thoroughly mixed to form a coatable composition. The composition was then coated onto a glass surface to form a film with a thickness of approximately 0.1–0.2 mm. The film was allowed to dry at room temperature until capable of forming a cohesive body, i.e., to a solvent content of from about 50% to about 70%. The resultant was rolled up and cut into many small pieces. Each piece was placed in a 0.63 mm diameter mold and compressed at 3,000 psi for 2 minutes to form 0.63 mm diameter cylinders, approximately 1.5 mm long and weighing about 0.85 mg to 1.05 mg, utilizing the compression molding device discussed hereinabove. The drug delivery devices were then exposed to gamma irradiation (60–90 KRads) for sterilization and stored in a refrigerator (4° C.) until used within 8 weeks.

EXAMPLE 6

Preparation of an Implantable Drug Delivery Device Comprising a Biodegradable Protein, an Additive and an Opioid Analgesic Implantable drug delivery devices comprising a biodegradable protein, an additive and an analgesic were made as follows. The opioid analgesic sufentanil citrate (obtained from National Institute on Drug Abuse), was desalted by adding ammonium hydroxide, extracted with n-hexane, collection of solvent and evaporation. The desalted sufentanil was reconstituted in 20 µl of 90% ethanol containing approximately 4,500,000 cpm of tritiated sufentanil (obtained from Jannsen Pharmaceutica, Belgium) to 2.0 mg/20 µl. The biodegradable protein SELP7 was dissolved in deionized water to 42.3 mg (SELP7)/200 µl and spread into a thin layer approximately 6 cm by 6 cm in area. Immediately thereafter, 22.5 mg of finely pulverized powder of an additive, the fatty acid dimer:sabacic acid (FAD:SA in 1:4 ratio) was added to the center of the protein solution area. Immediately thereafter, the sufentanil dissolved in the ethanol was added very slowly to the mound of FAD:SA over a period of a few minutes, i.e., from about 1 minute to about 5 minutes. After the sufentanil solution had soaked into the FAD:SA powder, the components were thoroughly mixed to form a coatable composition. The composition was then coated onto a glass surface to form a film with a thickness of approximately 0.1–0.2 mm. The film was allowed to dry at room temperature until capable of forming a cohesive body, i.e., to a solvent content of from about 50% to 70%. The resultant cohesive body was rolled up and placed in a 3.5 mm diameter mold and compressed at 8500 psi for 2 minutes to form a 3.5 mm diameter cylinder, approximately 4 mm long and weighing 54.1 mg, utilizing the compression molding device discussed hereinabove. This device was than exposed to gamma irradiation (60–90 KRads) for sterilization and stored in a refrigerator (4° C.) until used within 8 weeks.

EXAMPLE 7

Preparation of an Implantable Drug Delivery Device Comprising a Biodegradable Protein, an Additive and an Opioid Analgesic Implantable drug delivery devices comprising a biodegradable protein, an additive and an opioid analgesic were made as follows. The opioid analgesic sufentanil citrate (obtained from National Institute on Drug Abuse) was desalted by adding ammonium hydroxide, extracted with n-hexane, collection of solvent and evaporation. The desalted sufentanil was reconstituted in 20 µl of 90% ethanol containing approximately 3.500,000 cpm of tritiated sufentanil (obtained from Jannsen Pharmaceutica, Belgium) to 2.0 mg/20 µl. The biodegradable protein SELP7 was dissolved in deionized water to 15 mg (SELP7)/200 µl and spread into a thin layer approximately 6 cm by 6 cm in area. Immediately thereafter, 35.0 mg of finely pulverized powder of the additive glutamine, was added to the center of the protein solution area. Immediately thereafter, the sufentanil dissolved in the ethanol was added very slowly to the mound of glutamine over a time period of a few minutes. After the sufentanil solution had soaked into the glutamine powder, the components were thoroughly mixed to form a coatable composition. The composition was then coated onto a glass surface to form a film with a thickness of approximately 0.1–0.2 mm. The cast film was allowed to dry at room temperature until capable of forming a cohesive body, i.e., to a solvent content of from about 50% to 70%. The resultant cohesive body was rolled up and placed in a 3.5 mm diameter mold and compressed at 8500 psi for 2 minutes to form 3.5 mm diameter cylinders, approximately 2 mm long and weighing 39.1 mg, utilizing the compression molding device discussed hereinabove. This device was than exposed to gamma irradiation (60–90 KRads) for sterilization and stored in a refrigerator (4° C.) until used within 8 weeks.

EXAMPLE 8

Preparation of an Implantable Drug Delivery Device Comprising a Biodegradable Protein, an Additive and an Opioid Analgesic Implantable drug delivery devices comprising a biodegradable protein, an additive and an analgesic were made as follows. The opioid analgesic sufentanil citrate (obtained from National Institute on Drug Abuse), was desalted by adding ammonium hydroxide, extracted with n-hexane, collection of solvent and evaporation. The desalted sufentanil was reconstituted in 20 µl of 90% ethanol containing approximately 4,500,000 cpm of tritiated sufentanil (obtained from Jannsen Pharmaceutica, Belgium) to 2.0 mg/20 µl. The biodegradable protein SELP7 was dissolved in deionized water to 42.3 mg (SELP7)/200 µl and spread into a thin layer approximately 6 cm by 6 cm in area. Immediately thereafter, 22.5 mg of finely pulverized powder of an additive, the fatty acid dimer:sabacic acid (FAD:SA in 1:4 ratio) was added to the center of the protein solution area. Immediately thereafter, the sufentanil dissolved in the ethanol was added very slowly to the mound of FAD:SA over a period of a few minutes, i.e., from about 1 minute to about 5 minutes. After the sufentanil solution had soaked into the FAD:SA powder, the components were thoroughly mixed to form a coatable composition. The composition was then coated onto a glass surface to form a film with a thickness of approximately 0.1–0.2 mm. The film was allowed to dry at room temperature until capable of forming a cohesive body, i.e., to a solvent content of from about 50% to 70%. The resultant cohesive body was rolled up and placed in a 3.5 mm diameter mold and compressed at 8500 psi for 2 minutes to form 3.5 mm diameter cylinders, approximately 4 mm long and weighing 54.1 mg, utilizing the compression molding device discussed hereinabove. This device was than exposed to gamma irradiation (60–90 KRads) for sterilization and stored in a refrigerator (4° C.) until used within 8 weeks.

EXAMPLE 9

In Vitro Experiment with a Drug Delivery Device Comprising a Biodegradable Protein and an Enzyme A single cylinder piece, prepared as described above in Example 1, was added to a reaction chamber in a spectrophotometer containing xanthine, cytochrome C and other reactants according to previously described superoxide dismutase protocol (Sigma Quality Control Test Procedure EC 1.15.1.1 "Enzymatic Assay of Superoxide Dismutase") Enzyme activity of the enzyme xanthine oxidase in the piece was calculated at 0.0005 delta absorbance/min (absorbance measured at 550 nm where no enzyme activity produces 0.00000 change in absorbance). In comparison to a 0.01 unit solution of xanthine oxidase, which produced 0.0250 delta absorbance/min, the activity of the xanthine oxidase in the piece equaled 1% of the control solution in a time period of only 3 minutes. Thus, this result indicates that the diffusional barrier provided by the biodegradable polymeric matrix of the drug delivery device allows the enzyme to remain active from within the drug delivery device.

EXAMPLE 10

In Vitro Experiment with a Drug Delivery Device Comprising a Biodegradable Protein and an Enzyme In this assay system, xanthine oxidase, xanthine, cytochrome C and other reactants were added together to produce a delta absorbance of 0.0250/min. (Sigma Quality Control Test Procedure EC 1.15.1.1 "Enzymatic Assay of Superoxide Dismutase"). SOD activity is measured as the inhibition of the rate of reduction of ferricytochrome C by superoxide, observed at 550 nm, as described by J. McCord, I. J. Biol. Chem., 244, 6049 (1969). The addition of a SOD containing piece, produced as described in Example 2 hereinabove, reduced the reaction to 0.0233 delta absorbance/min. Since 1 unit SOD will inhibit the reaction of cytochrome C by 50% in a coupled system using xanthine oxidase, it can be determined that the activity of the SOD pellet equaled 0.14 units of SOD. This activity represents about 2% of the SOD loaded into the biodegradable protein matrix of the drug delivery device. Thus, this result indicates that the diffusional barrier provided by the biodegradable polymeric matrix of the drug delivery device allows the enzyme to remain active from within the drug delivery device.

EXAMPLE 11

In Vivo Experiment with a Drug Delivery Device Comprising a Biodegradable Protein and Liposheres The drug delivery devices comprising a biodegradable protein and liposheres produced according to Example 3 hereinabove were surgically implanted next to the sciatic nerve of one young adult male Sprague Dawley rat (200–250 g) as described previously by Masters in D. B. Masters et al., *Anesthesiol.*, 79, 340 (1993). Briefly, the rat was anesthetized with 50–75 mg/kg pentobarbital to allow faster recovery for behavioral measurements. Bilateral posterolateral incisions were made in the upper thighs and the sciatic nerves were visualized with care to avoid direct trauma. Drug delivery devices prepared as described in Example 3 were injected around the nerve on one leg, while no drug delivery device was inserted in the contralateral leg to serve as a control. The fascia and muscle surrounding the administration site was closed over to partially restrict egress of the drug delivery device and the entire wound area was lavaged with 0.5 cc of an antibiotic solution (5000 units/ml penicillin G sodium and 5000 µg/ml streptomycin sulfate). The experimenter performing subsequent thermal sensitivity testing and motor capacity tests was unaware of which side received the drug delivery device and which side received nothing.

After having the drug delivery device implanted, the rat was subjected to periodic thermal sensitivity and motor capacity testing according to the protocol described above. As shown in Table 1, the drug delivery devices so implanted produced at least 4 days of local anesthetic block, i.e., a reduction in thermal sensitivity with a concurrent reduction in motor capacity tests compared to the control leg.

TABLE 1

In vivo local anesthetic block produced by a drug delivery device comprising liposheres (they themselves break down within the matrix)

| Time (hr) | Thermal Sensitivity Tests | Motor capacity (weight bearing) |
| --- | --- | --- |
| 0 | 100% ± 5% | 100% ± 2% |
| 2 | 427% | 41% |
| 4 | 560% | 44% |
| 20 | 196% | 56% |
| 26 | 216% | 62% |
| 42 | 195% | 79% |
| 48 | 180% | 77% |
| 96 | 126% | 75% |
| 120 | 105% | 76% |

EXAMPLE 12

In Vivo Experiment with a Drug Delivery Device Comprising a Biodegradable Protein and two Pharmacologically Active Agents Three "first drug delivery devices" prepared according to Example 4, i.e. comprising 6 mg of capsaicin and 6 mg dexamethasone were implanted next to the sciatic nerve of one young adult male Sprague Dawley rat using the procedures described above in Example 7. The rat was monitored for a period of 624 hours. The results of this experiment are shown in Table 2, below. The first drug delivery devices produced strong thermal sensitivity, but no reduced motor capacity, for 6 days. Because the rat showed some weight loss the devices were removed on day 6. The rat continued to show a strong reduction in thermal sensitivity for the next 14 days before returning to baseline response levels. In comparison to the contralateral control leg no reduced motor capacity was detected. Therefore, a very strong sensory neural blockade (analgesia) was obtained by placement of these matrices without associated motor deficits.

TABLE 2

In vivo local anesthetic block produced by a drug delivery device incorporating 6 mg Capsaicin and 6 mg Dexamethasone

| Time (hr) | Thermal Sensitivity Tests (experimental/control) | Motor Capacity (weight bearing) |
| --- | --- | --- |
| −48 | 0.98 | nd |
| −24 | 0.98 | 0.99 |
| −1 | 1.02 | 1.01 |
| 2 | 2.47 | nd |
| 4 | 2.04 | 0.97 |
| 24 | 1.80 | 0.95 |
| 48 | 2.72 | 1.01 |
| 96 | 1.94 | 0.86 |
| 144 | 2.86 | 0.91 |
| 168 | 2.34 | 0.97 |
| 192 | 2.19 | 0.99 |
| 216 | 3.04 | 1.00 |
| 264 | 2.59 | 1.00 |
| 288 | 1.76 | 1.05 |
| 312 | 1.58 | 0.99 |
| 318 | 2.55 | 0.99 |
| 336 | 2.06 | 1.01 |
| 360 | 1.65 | 0.98 |
| 384 | 1.65 | 0.99 |
| 432 | 2.16 | 0.99 |
| 456 | 1.35 | 1.01 |
| 480 | 0.92 | 0.99 |
| 504 | 1.10 | 1.01 |
| 528 | 0.98 | 1.02 |
| 552 | 1.38 | 1.00 |
| 624 | 1.07 | 1.01 |

Five "second drug delivery devices", i.e., comprising 6 mg of capsaicin and 1.2 mg dexamethasone, prepared as described above in Example 4 were implanted next to the sciatic nerve of individual rats, where they produced a strong reduction in thermal sensitivity with no concurrent reduction in motor capacity for several days to weeks. All 5 rats showed some weight loss, but far less than that observed with implantation of the first devices.

The results of this experiment are shown in Table 3, below. As shown, a very strong reduction in thermal sensitivity was obtained by implantation of these devices without a concurrent reduction in motor capacity. As is shown, all rats showed similar effects with various durations, i.e., no rats showed motor deficits. Lower doses of capsaicin and dexamethasone showed similar results.

TABLE 3

In vivo local anesthetic block produced by a drug delivery device incorporating 6 mg Capsaicin and 1.2 mg Dexamethasone

| Time (hr) | Thermal Sensitivity Tests | Motor Capacity (weight bearing) |
|---|---|---|
| −48 | 1.13 | 1.00 |
| −24 | 0.96 | 0.99 |
| −1 | 1.02 | 1.02 |
| 2 | 2.72 | 1.02 |
| 4 | 3.77 | 1.00 |
| 24 | 2.50 | 1.17 |
| 48 | 2.86 | 1.00 |
| 96 | 2.72 | 0.96 |
| 120 | 1.78 | 1.01 |
| 144 | 3.05 | 1.01 |
| 168 | 2.06 | 0.98 |
| 192 | 1.82 | 1.00 |
| 216 | 1.74 | 1.03 |
| 288 | 3.14 | 1.00 |
| 312 | 2.88 | 1.00 |
| 336 | 2.17 | 1.01 |
| 360 | 1.83 | 0.99 |
| 456 | 1.33 | |
| 480 | 1.22 | 0.99 |
| 504 | 1.85 | 1.01 |
| 528 | 1.72 | 0.99 |
| 552 | 1.92 | 1.01 |
| 624 | 2.42 | 0.99 |
| 672 | 2.13 | 0.97 |
| 792 | 1.50 | 1.01 |
| 840 | 1.24 | 0.99 |
| 888 | 1.49 | 1.01 |
| 984 | 1.36 | |

EXAMPLE 13

In Vitro Experiment with an Injectable Drug Delivery Device Comprising a Biodegradable Protein, an Additive and an Opioid Analgesic Four pellets, prepared as described in Example 5, were each added to separate glass vials treated with a silicone coating (commercially available under the trade designation "Sigmacote" from Sigma Chemical Company, St. Louis, Mo.) to prevent loss of tritiated sufentanil. The pellets were added to the glass vials filled with 15 ml of 0.1 M phosphate buffered saline (pH 7.4), and then were incubated at 37° C. with agitation. At specific time intervals, 20 μl samples were taken in triplicate from each glass vial and measured for radioactive sufentanil using a scintillation counter. As shown in FIG. 4, each of the four matrices produced at least 9 days of sufentanil release following a first order release rate.

EXAMPLE 14

In Vitro Experiment with an Implantable Drug Delivery Device Comprising a Biodegradable Protein, an Additive and an Opioid Analgesic A single pellet, prepared as described in Example 6 was added to a glass vial treated with a silicone coating (commercially available under the trade designation "Sigmacote" from Sigma Chemical Company, St. Louis, Mo.) to prevent loss of tritiated sufentanil. The glass vial was filled with 15 ml of 0.1 M phoshate buffered saline (pH 7.4), and incubated at 37° C. with agitation. At specific time intervals, 20 μl samples were taken in triplicate and measured for radioactive sufentanil using a scintillation counter. As shown in Table 4, this 3.5 mm diameter cylinder matrix produced at least 75 days of sufentanil release following near zero-order release rate kinetics.

TABLE 4

In Vitro Release Study of implantable Drug Delivery Device comprising a Biodegradable Protein, an Additive and an Opioid Analgesic

| Time (hr) | Scintillation Counts (cpm) | Cumulative Release (%)* |
|---|---|---|
| 1 | 59050 | 1.48 |
| 4 | 26883 | 3.17 |
| 10 | 228667 | 5.72 |
| 28 | 263650 | 6.59 |
| 49 | 415150 | 10.38 |
| 73 | 455000 | 11.38 |
| 120 | 561517 | 14.04 |
| 200 | 583333 | 14.58 |
| 251 | 619283 | 15.48 |
| 299 | 653517 | 16.34 |
| 428 | 751517 | 18.79 |
| 603 | 901483 | 22.54 |
| 793 | 1281183 | 32.03 |
| 1030 | 1645650 | 41.14 |
| 1199 | 1810450 | 45.26 |
| 1368 | 2093083 | 52.33 |
| 1536 | 2532467 | 63.31 |
| 1704 | 3205867 | 80.15 |
| 1899 | 3446133 | 86.15 |
| 2003 | 3528650 | 88.22 |
| 2239 | 3689717 | 92.24 |

*Based on total expected counts = 4,500,000

EXAMPLE 15

In Vitro Experiment with an Implantable Drug Delivery Device Comprising a Biodegradable Protein, an Additive and an Opioid Analgesic A single pellet, prepared as described in Example 7 was added to a glass vial treated with a silicone coating (to prevent loss of tritiated sufentanil commercially available under the trade designation "Sigmacote," from Sigma Chemical Company, St. Louis, Mo.). The glass vial was filled with 15 ml of 0.1 M phosphate buffered saline (pH 7.4), and incubated at 37° C. with agitation. At specific time intervals. 20 μl samples were taken in triplicate and measured for radioactive sufentanil using a scintillation counter. As shown in Table 5, this 3.5 mm diameter cylinder matrix produced approximately 2 days of sufentanil release. The addition of glutamine facilitated the release of sufentanil out of the matrix.

TABLE 5

In Vitro Release Study of Implantable Drug Delivery Device comprising a Biodegradable Protein, an Additive and an Opioid Analgesic

| Time (hr) | Scintillation Counts (cpm) | Cumulative Release (%)* |
|---|---|---|
| 1 | 59050 | 1.48 |
| 2 | 671133 | 19.29 |
| 4 | 1495667 | 43.00 |
| 10 | 2230283 | 64.11 |
| 28 | 2908267 | 83.61 |
| 49 | 3346450 | 96.20 |
| 73 | 3422867 | 98.40 |
| 120 | 3439183 | 98.87 |
| 200 | 3430783 | 98.63 |
| leftover cpm in pellet | 47792 | |
| *total cpm | 3478575 | |

EXAMPLE 16

In Vivo Experiment with Drug Delivery Devices Comprising a Biodegradable Protein, an Additive and an Opioid Analgesic The drug delivery devices comprising a protein (SELP7), an additive (FAD:SA), and an opioid analgesic (sufentanil), produced according to Example 5 hereinabove, were injected into the left side of the epidural space adjacent to spinal cord at the fifth lumbar vertebrae in 2 young adult male Sprague Dawley rats. All rats underwent pretesting for thermal sensitivity tests and motor capacity tests as described hereinabove. The rats were anesthetized with halothane (4% induction, 2% maintenance) and prepared for spinal injection by creating a sterile surgical field over the dorsal aspect of the lower lumber vertebral column. The placement of the drug delivery devices was in close proximity to the left dorsal root ganglion and nerve root at lumbar level 5, which is associated with nerve input from the left hind paw via the sciatic nerve. After needle insertion validation, drug delivery devices were loaded into an 18 gauge Tuohy epidural needle for injection, most commonly used by anesthesiologists for spinal administration of drug solutions. Before injection of the implants into the epidural space, validation of the space was carried out by x-ray techniques to locate the tip of the needle using an opaque catheter and small x-ray machine. Aspiration of the space occupied by the catheter was also used to validate that it was in the dry epidural space and not the subdural space which is filled with cerebrospinal fluid. The dosage delivered from the drug delivery devices was adjusted by administering more than one implant into the epidural space. To test for a dose response effect, rat F043 received two drug delivery devices containing sufentanil and rat F045 received 6 drug delivery devices containing sufentanil. In this experiment a third rat, F046, was used as a control and received two control devices via the same epidural administration technique. The control devices were made by the same coatable composition technique using the same quantities of biodegradable protein (SELP7), additive FAD:SA, deionized water and ethanol without the presence of sufentanil. The results of this experiment are shown in Table 6, below, where time is in hours relative to epidural administration of the drug delivery devices. Rats F043 and F045 showed prolonged opioid analgesia for approximately 9–12 days in thermal sensitivity tests, performed as described hereinabove, i.e., increased latency (seconds) to remove their paws from a heated surface. Epidural injections of sufentanil citrate at highest possible doses without becoming toxic (5–7 μg/kg), only produced 2 hours of measurable effects to thermal sensitivity testing in three control rats.

TABLE 6

In Vivo Thermal Sensitivity Latency Tests for Drug Delivery Devices Comprising a Protein, and a Polyanhydride Copolymer with and without an Opioid

| Time (hr) | F043 (2 devices) | | F045 (6 devices) | | F046 (2 control devices) | |
| --- | --- | --- | --- | --- | --- | --- |
| | Left Paw | Right Paw | Left Paw | Right Paw | Left Paw | Right Paw |
| −48 | 2 | 1.8 | 1.9 | 2 | 2.5 | 2.4 |
| −24 | 2.4 | 2.1 | 2 | 2 | 2.7 | 2.3 |
| −1 | 1.8 | 1.9 | 1.9 | 2.1 | 2.2 | 2.2 |
| 1 | 2.8 | 2.4 | 12 | 3.7 | 3.5 | 3.2 |
| 4 | 3 | 2 | 5.6 | 2.7 | 2.9 | 2.7 |
| 22 | 2.8 | 2.1 | 5.7 | 2.9 | 2.3 | 2.2 |
| 46 | 3.4 | 2.1 | 8.4 | 3 | 2.3 | 2.4 |
| 74 | 2.9 | 2.1 | 7.1 | 2.5 | nd | nd |
| 119 | 2.8 | 1.8 | 6.8 | 2.4 | 2.5 | 2.4 |
| 144 | nd | nd | 9.7 | 2 | 2.4 | 2.3 |
| 166 | nd | nd | 7.5 | 2.2 | 2.5 | 2.4 |
| 189 | 2.7 | 1.9 | 10.1 | 2.1 | nd | nd |
| 211 | 3.1 | 2.1 | 5.6 | 2.5 | nd | nd |
| 289 | 2.9 | 2.3 | 2.6 | 1.8 | nd | nd |
| 314 | 2.8 | 2 | 2.3 | 1.9 | nd | nd |

TABLE 6-continued

In Vivo Thermal Sensitivity Latency Tests for Drug Delivery Devices Comprising a Protein, and a Polyanhydride Copolymer with and without an Opioid

| Time (hr) | F043 (2 devices) | | F045 (6 devices) | | F046 (2 control devices) | |
| --- | --- | --- | --- | --- | --- | --- |
| | Left Paw | Right Paw | Left Paw | Right Paw | Left Paw | Right Paw |
| 337 | 2.5 | 1.8 | 1.9 | 1.9 | nd | nd |
| 391 | 3 | 2.1 | 1.8 | 1.9 | nd | nd |
| 435 | 2 | 2.1 | 1.8 | 1.7 | nd | nd |
| 457 | 2.1 | 1.8 | 1.8 | 1.9 | nd | nd |
| 482 | nd | nd | 2 | 2 | nd | nd |

*nd = not determined; Testing was stopped after rat returned to pre-device response level.

What is claimed is:

1. A method of making a solvated drug delivery device, comprising the steps of:
  (a) preparing a coatable composition comprising one or more biodegradable polymeric materials, one or more pharmacologically active agents, and one or more biocompatible solvents;
  (b) coating the composition to form a film;
  (c) partially drying the coated film until the coated film can be formed into a cohesive body;
  (d) forming said cohesive body; and
  (e) compressing the cohesive body to form a drug delivery device.

2. The method of claim 1, wherein the biodegradable polymeric material comprises a biodegradable protein.

3. The method of claim 2, wherein the biodegradable protein comprises a naturally occurring protein.

4. The method of claim 3, wherein the naturally occurring protein comprises elastin.

5. The method of claim 2, wherein the biodegradable protein comprises a genetically engineered protein.

6. The method of claim 5, wherein the genetically engineered protein comprises silk-like blocks and elastin-like blocks.

7. The method of claim 3, wherein the drug delivery device further comprises an additive to enhance the release characteristics of the pharmacologically active agent.

8. The method of claim 7, wherein the additive comprises one or more fatty acid monomers.

9. The method of claim 8, wherein the fatty acid monomers comprise an erucic dimer and sebacic acid.

10. The method of claim 9, wherein the ratio of fatty acid dimer to sabacic acid is 1:4 based upon weight.

11. The method of claim 10, wherein the biodegradable polymeric material comprises a genetically engineered protein comprising silklike blocks and elastinlike blocks and wherein the ratio of the genetically engineered protein to the fatty acid dimer:sabacic acid copolymer is about 2:1, based upon weight.

12. The method of claim 1, wherein the cohesive body is compressed at a pressure of from about 100 psi to about 30,000 psi for a time period of from about 10 seconds to about 48 hours.

13. The method of claim 12, wherein the cohesive body is compressed at a pressure of from about 1000 psi to about 4000 psi for a time period of from about 1 minute to about 60 minutes.

14. The method of claim 1, wherein the cohesive body is compressed into the form of a cylinder.

15. The method of claim 14, wherein the cylinder is subsequently cut into discs.

16. The method of claim 1, wherein the pharmacologically active agent comprises a corticosteroid.

17. The method of claim 16, wherein the pharmacologically active agent comprises dexamethasone.

18. The method of claim 1, wherein the pharmacologically active agent comprises a neurotoxin.

19. The method of claim 20, wherein the neurotoxin is capsaicin.

20. The method of claim 1, wherein the pharmacologically active agent comprises an opioid analgesic.

21. The method of claim 20, wherein opioid analgesic comprises sufentanil.

22. The method of claim 1, wherein the pharmacologically active agent is a local anesthetic.

23. The method of claim 22, wherein the local anesthetic comprises bupivacaine, lidocaine, or a combination thereof.

24. The method of claim 1, wherein the pharmacologically active agent comprises an enzyme.

25. The method of claim 24, wherein the coatable composition further comprises an amount of an enzyme substrate.

26. The method of claim 1, wherein the drug delivery device contains a second, migration-vulnerable drug delivery device that incorporates the pharmacologically active agent.

27. The method of claim 26, wherein the migration-vulnerable drug delivery device comprises a plurality of lipospheres homogeneously dispersed within the drug delivery device.

28. The method of claim 27, wherein the migration-vulnerable drug delivery device comprises a plurality of microspheres homogeneously dispersed within the drug delivery device.

29. The method of claim 1, wherein the pharmacologically active agent is substantially homogeneously distributed within the drug delivery device.

30. The method of claim 1, wherein the biodegradable polymeric material comprises at least one polymeric material that degrades quickly and at least one polymeric material that degrades slowly relative to one another.

31. The method of claim 1, wherein the coated film is dried until the solvent content is approximately 50% to 70%.

32. The method of claim 1, wherein the drug delivery device includes a solvent content of approximately 30% to 60%.

33. The method of claim 32, wherein the drug delivery device includes a solvent content of approximately 40% to 50%.

* * * * *

UNITED STATES PATENT AND TRADEMARK OFFICE
CERTIFICATE OF CORRECTION

PATENT NO. : 6,342,250 B1
DATED : January 29, 2002
INVENTOR(S) : David B. Masters It is certified that error appears in the above-identified patent and that said Letters Patent is hereby corrected as shown below:

<u>Column 10,</u>
Line 56, "preferably that" should be changed to -- preferably be that --.

<u>Column 16,</u>
Line 27, "denature them,." should be changed to -- denature them. --.
Line 29, "agents may exert" should be changed to -- agents to exert --.

<u>Column 18,</u>
Line 26, "pharaincologically active agent" should be changed to -- pharmacologically active agent --.
Line 37, "400 million" should be changed to -- 400 million. --.

<u>Column 31,</u>
Line 7, "The method of claim 20" should be changed to -- The method of claim 18. --.

Signed and Sealed this

First Day of April, 2003

JAMES E. ROGAN
*Director of the United States Patent and Trademark Office*